US008008305B2

(12) United States Patent
Galley et al.

(10) Patent No.: US 8,008,305 B2
(45) Date of Patent: Aug. 30, 2011

(54) TAAR1 LIGANDS

(75) Inventors: Guido Galley, Rheinfelden (DE);
Katrin Groebke Zbinden, Liestal (CH);
Roger Norcross, Olsberg (CH); Henri Stalder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 230 days.

(21) Appl. No.: 12/180,571

(22) Filed: Jul. 28, 2008

(65) Prior Publication Data
US 2009/0036452 A1 Feb. 5, 2009

(30) Foreign Application Priority Data
Aug. 3, 2007 (EP) .................... 07113752

(51) Int. Cl.
A61K 31/496 (2006.01)
C07D 213/82 (2006.01)
C07D 401/12 (2006.01)
C07D 405/12 (2006.01)
A61K 31/166 (2006.01)
A61K 31/444 (2006.01)
A61K 31/4439 (2006.01)
A61K 31/4402 (2006.01)
A61K 31/4545 (2006.01)
A61K 31/44 (2006.01)
A61K 31/404 (2006.01)
A61K 31/435 (2006.01)
C07C 231/02 (2006.01)
C07D 233/66 (2006.01)
C07D 233/64 (2006.01)
C07D 413/12 (2006.01)

(52) U.S. Cl. .............. 514/253.11; 514/253.13; 544/364; 544/365; 544/131; 544/383; 544/393; 546/233; 546/234; 546/276.4; 546/277.4; 546/284.1; 548/309.7; 564/185

(58) Field of Classification Search .................. None
See application file for complete search history.

(56) References Cited

U.S. PATENT DOCUMENTS

| 2,161,938 | A | 6/1939 | Sonn |
| 2,457,047 | A | 12/1948 | Kyrides |
| 2,731,471 | A | 1/1956 | Synerholm et al. |
| 2,744,909 | A | 5/1956 | Speeter |
| 2,744,910 | A | 5/1956 | Speeter |
| 2,778,836 | A | 1/1957 | Morren |
| 2,919,274 | A | 12/1959 | Faust et al. |
| 3,161,653 | A | 12/1964 | Fruhstorfer et al. |
| 3,354,175 | A | 11/1967 | Fruhstorfer et al. |
| 3,377,247 | A | 4/1968 | Elbe |
| 3,480,630 | A | 11/1969 | Stahle et al. |
| 3,586,695 | A | 6/1971 | Wysong et al. |
| 3,622,579 | A | 11/1971 | Stahle et al. |
| 3,660,423 | A | 5/1972 | Wysong et al. |
| 3,758,476 | A | 9/1973 | Rippel et al. |
| 3,818,035 | A | 6/1974 | Binon et al. |
| 3,818,094 | A | 6/1974 | Stahle et al. |
| 3,992,403 | A | 11/1976 | Roebke |
| 4,125,620 | A | 11/1978 | Stahle et al. |
| 4,146,647 | A | 3/1979 | Lafon |
| 4,323,570 | A | 4/1982 | Stenzel et al. |
| 4,665,095 | A | 5/1987 | Winn et al. |
| 4,734,419 | A | 3/1988 | Hashimoto et al. |
| 5,610,174 | A | 3/1997 | Craig et al. |
| 5,658,938 | A | 8/1997 | Geerts et al. |
| 5,866,583 | A | 2/1999 | Guerry et al. |
| 2002/0019390 | A1 | 2/2002 | Wong et al. |
| 2003/0181354 | A1 | 9/2003 | Abdulrazik |
| 2003/0236259 | A1* | 12/2003 | Hohlweg et al. .............. 514/242 |
| 2003/0236274 | A1 | 12/2003 | Tasaka et al. |
| 2006/0189626 | A1* | 8/2006 | Hoffmann et al. ........ 514/253.01 |
| 2007/0249579 | A1* | 10/2007 | Wang et al. .............. 514/210.21 |

FOREIGN PATENT DOCUMENTS
CA  2246027  2/2000
(Continued)

OTHER PUBLICATIONS

Deutch et al., (1999) Neurotransmitters. In Fundamental Neuroscience ($2^{nd}$ ed.) pp. 193-234, Academic Press.
(Continued)

Primary Examiner — Emily Bernhardt
(74) Attorney, Agent, or Firm — George W. Johnston; Patricia S. Rocha-Tramaloni; Kimberly J. Prior

(57) ABSTRACT

The invention relates to a compound of formula

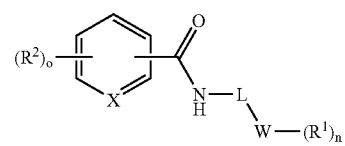

I wherein
$R^1$, $R^2$, X, L, W, n, and o are defined herein and
to pharmaceutically suitable acid addition salts thereof, with the exception of the following compounds
6-(4-methyl-piperazin-1-yl)-N-phenethyl-nicotinamide (CAS 199478-31-4),
N-(3,4-dichloro-benzyl)-3-fluoro-benzamide (CAS 424815-98-5),
N-(4-chloro-benzyl)-3-fluoro-benzamide (CAS 544661-83-8),
N-(3-chloro-benzyl)-3-fluoro-benzamide (CAS 796051-07-5), and
N-phenethyl-6-phenylamino-nicotinamide (CAS 571913-74-1).
The compounds of formula I have a good affinity to the trace amine associated receptors (TAARs), especially for TAAR1 and are useful for the treatment of CNS disorders.

10 Claims, No Drawings

FOREIGN PATENT DOCUMENTS

| | | |
|---|---|---|
| DE | 1695005 | 2/1971 |
| DE | 3133887 | 3/1983 |
| EP | 0 024 829 | 3/1981 |
| EP | 0086043 | 8/1983 |
| EP | 0 125 410 | 11/1984 |
| EP | 0 166 937 | 1/1986 |
| EP | 0 331 374 | 9/1989 |
| EP | 0 424 059 | 4/1991 |
| EP | 0 857 483 | 8/1998 |
| EP | 0 924 209 | 6/1999 |
| EP | 1 103 243 | 5/2001 |
| EP | 1 413 576 | 4/2004 |
| EP | 1449841 | 8/2004 |
| EP | 1669348 | 6/2006 |
| ES | 323 985 | 12/1966 |
| FR | 6 551 | 12/1968 |
| GB | 877306 | 9/1961 |
| GB | 1016514 | 1/1966 |
| WO | WO 96/22768 | 8/1996 |
| WO | WO 97/12874 | 4/1997 |
| WO | WO 98/12183 | 3/1998 |
| WO | WO 01/30762 | 5/2001 |
| WO | WO 01/81334 | 11/2001 |
| WO | WO 02/22801 | 3/2002 |
| WO | WO 02/40453 | 5/2002 |
| WO | WO 02/076950 | 10/2002 |
| WO | WO 03/092374 | 11/2003 |
| WO | WO 2004/014898 | 2/2004 |
| WO | WO 2006/014168 | 2/2006 |
| WO | WO 2006/107923 | 10/2006 |
| WO | WO 2006/119411 | 11/2006 |
| WO | WO 2007/024944 | 3/2007 |
| WO | WO 2007/071358 | 6/2007 |
| WO | WO 2007/098352 | 8/2007 |

OTHER PUBLICATIONS

Wong, et al., (2001) Nat. Rev. Neurosci. 2, pp. 343-351.
Carlsson. et al. (2001) Annu Rev. Pharmacol. Toxicol. 41, pp. 237-260.
Tuite et al., (2003) Expert Opin. Investig. Drugs 12, pp. 1335-1352.
Castellanos et al., (2002) Nat. Rev. Neurosci. 3, pp. 617-628.
Usdin, E.; Sandler, M.; Editors. Psychopharmacology Series, vol. 1: Trace Amines and the Brain. [Proceedings of a Study Group at the 14th Annual Meeting of the American College of Neuropsychoparmacology, San Juan, Puerto Rico](1976), pp. 1-281.
Lindemann et al., (2005) Trends in Pharmacol. Sci. 26, pp. 274-281.
Branchek et al., (2003) Curr. Opin. Pharmacol. 3, pp. 90-97.
Premont et al. (2001) Proc. Natl. Acad. Sci. U. S. A. 98, pp. 9474-9475.
Mousseau et al., (1995) Prog. Brain Res. 106, pp. 285-291.
McCormack et al. (1986) J. Neurosci. 6, pp. 94-101.
Dyck, L. E. (1989) Life Sci. 44, pp. 1149-1156.
Parker, et al. (1988) J. Pharmacol. Exp. Ther. 245, pp. 199-210.
Lindemann et al. (2005) Genomics 85, pp. 372-385.
Moormann, et al., (1990) J. Med. Chem. pp. 614-626.
Hlasta et al., (1987) vol. 30, J. Med. Chem. pp. 1555-1562.
Dash et al., (2006) J. Heterocyclic Chem. pp. 401-404.
Gentili et al., (2004) J. Med. Chem. vol. 47 pp. 6160-6173.
Dias et al. (2005) J. Med. Chem. vol. 40 pp. 1206-1213.
Pigini et al., (1987) Eur. J. Med. Chem. vol. 22 pp. 273-276.
Wu et al., Synthesis (2003) pp. 1657-1660.
Fujioka et al., (2005) Tetrahedron Lett. vol. 46, pp. 2197-2199.
Ishihara et al., Synlett (2006) pp. 227-230.
Pinza et al. (1976) Heterocycles, vol. 4 pp. 1699-1706.
Kornicka et al. (2006) Heterocycles vol. 68 pp. 687-699.
Kosasayama et al., (1979) Chem. Pharm. Bull. vol. 27 pp. 831-840.
Lloyd et al., (1980) Tetrahedron vol. 36, pp. 2675-2679.
Flippin et al., Tetrahedron Letters, vol. 34, pp. 3255-3258 (1993).
Liebigs, Ann. Chem. pp. 2061-2071 (1980), Bestmann et al.
Huh et al., Tetrahedron, vol. 58, pp. 9925-9932 (2002).
Huh et al., Tetrahedron, vol. 60, pp. 9857-9862 (2004).
Law et al., J. Med. Chem. vol. 41, pp. 2243-2251 (1998).
Debernardis et al., J. Med. Chem. vol. 29, pp. 1413-1417 (1986).
Mohammadpoor-Baltork, Bull. Korean Chem. Soc. vol. 24, p. 1354-1356 (2003).
Abdollahi-Alibeik et al., Bioorg. Med. Chem. Lett. vol. 14, pp. 6079-6082 (2004).
Amemiya, Synth. Commun. vol. 20, pp. 2483-2489 (1990).
Ohta, Chem. Pharm. Bull. vol. 35, pp. 1058-1069 (1987).
Olah, Synlett pp. 647-650 (1992).
Katz et al., Tetrahedron, vol. 45, pp. 1801-1814 (1989).
Wentland et al., J. Med. Chem. vol. 30, pp. 1482-1489 (1987).
Campos et al., Heterocycles, vol. 40, p. 841-849 (1995).
Ohta, Synthesis, pp. 78-81 (1990).
Mancuso et al., J. Org. Chem. vol. 43, pp. 2480-2482 (1978).
Mohammadpoor-Baltork, Synlett, pp. 2803-2805 (2004).
Cahiez et al., Synthesis, pp. 2138-2144 (1999).
Evans et al., Tetrahedron Lett. vol. 39, pp. 2937-2940 (1998).
Nakamura et al., J. Chem. Soc. Perkin Trans. 1, pp. 1061-1066 (2002).
Turner, et al. (1991) J. Org. Chem. vol. 56, pp. 5739-5740.
Zhang et al., J. Med. Chem. 1997, 40, pp. 3014-3024.
Reimann et al., Arch. Pharm. 1989, vol. 322, pp. 363-367.
Klapars, et al., J. Am. Chem. Soc. 2001, vol. 123, pp. 7727-7729.
Anderson, et al., Tetrahedron, 2002, vol. 58, pp. 8475-8481.
Touzeau et al., J. Med. Chem. 2003, vol. 46, pp. 1962-1979.
Altenbach et al., Synthesis and Structure-Activity Studies on N-[5-(1H-Imidazol-4-yl)-5,6,7,8-tetrahydro-1-naphthalenyl]methanesulfonamide, an Imidasole-Containing $\alpha_{1A}$-Adrenoceptor Agonist, J. Med. Chem. (2004), 47: 3220-3235.
Amemiya et al., Synthesis and α-Adrenergic Activities of 2-and 4-Substituted Imidazoline and Imidazoline Analogues, J. Med. Chem. (1992), 35:750-755.
Bagley et al., Synthesis and $\alpha_2$-Adrenegeric Activities of Imidazole and Imidazolidine Analogues: In Vitro and In Vivo Selectivity, Medicinal Chemistry Research (1994), 4:346-364.
Branchek et al., Trace amine receptors as targets for novel therapeutics: legend, myth and fact, Curr. Opin. Phamacol. (2003), 3:90-97.
Bunzow et al., Amphetamine, 3,4-Methylenedioxymethamphetamine, Lysergic Acid Diethylamide, and Metabolites of the catecholamine Neurotransmitters Are Agonists of a Rat Trace Amine Receptor, Molecular Pharmacology (2001), 60: 1181-1188.
Carroll et al., In Vitro and In Vivo Characterization of Alpha-1A Selective Agonists and Their Utility for Stress Incontinence, Med. Chem. Res. (2004), 13:134-148.
De Bernardis et al., Conformationally Defined Adregernic Agents. 5. Resolution, Absolute Configuration, and Pharmacological Characterization of the Enantiomers of 2-(5,6-Dihydroxy-1,2,3,4-tetrahydro-l-naphthyl)imidazoline: A Potent Agonist at a α—Adrenoceptors, J. Med. Chem. (1987), 30:1011-1017.
Faust et al., Antihypertensive Agents: Derivatives of 2-Imidazoline and 1,4,5,6-Tetrahydropyrimidine, J. Org. Chem. (1961), 26: 4044-4047.
Hirashima et al., Three-Dimensional Common-Feature Hypotheses for Octopamine Agonist 2-(Arylimino)imidazolidines, Bioorganic & Medicinal Chemistry (2002), 10:117-123.
Holt, A., Imidazoline binding sites on receptors and enzymes:Emerging targets for novel antidepressant drugs?, Journal of Psychiatry & Neuroscience (2003), 28:409-414.
Jetter et al., Synthesis of 4-Substituted Imidazoles via Palladium-Catalyzed Cross-Coupling Reactions, Synthesis (1998), 829-831.
Law et al., Benzylimidazolines as h5-$HT_{1B/1D}$ Serotonin Receptor Ligands: A Structure-Affinity Investigation, J. Med. Chem. (1998), 41:2243-2251.
Lee et al., 4-[(N-Imidazol-2-ylmethyl)aniline]pyranopyridine Analogs as Novel Anti-Angiogenic Agents, Bull. Korean Chem. Soc. (2005), 25: 619-628.
Matsunaga et al., $C_{17,20}$inhibitors. Part 2: Design, synthesis and structure-activity relationships of (2-naphthylmethyl)-1H-imidazoles as novel $C_{17,20}$-lyase inhibitors, Bioorganic & Medicinal Chemistry (2004), 4314.
Matsunaga et al., Synthetic studies on (1S)-6,7-dimethoxy-2-naphthyl)-1-(1H-imidazol-4-y1)2-methylpropan-l-ol as a selective $C_{17,20}$-lyase inhibitor, Tetrahedron: Asymmetry (2004), 15: 2021-2028.

McLennan, P;L., The Hypothermic Effect of Clonidine and Other Imidazolidines in Relation to their Ability to Enter the Central Nervous System in Mice, European Journal of Pharmacology (1981), 69:477-482.

Nathanson, J.A.,Phenyliminoimidazolines: Characterization of a Class of Potent Agonists of Octopamine-Sensitive Adenylate Cylcase and Their Use in Understanding the Pharmacology of Octopamine Receptors, Amer. Soc. Pharmacology (1985), 28:254-268.

Ojida et al., Sterocontrolled synthesis of (1S)- 1 -(1H-imidazol-4-yl)-1-(6-methoxy-2-napthyl)-2-methylpropan-1-ol as a potent $C_{17,20}$-lyase inhibitor,Tetrahedron: Asymmetry (2004), 15: 1555-1559.

Olmos et al., Imidazolines stimulate release of insulin from RIN-5AH cells independently from imidazoline $I_1$ and $I_2$ receptors, European Journal of Pharmacology (1994), 262: 41-48.

Prisinzano et al., 2-(aniline)imidazolines and 2-(benzyl)imidazoline derivatives as $h5$-HT-$_{1D}$ serotonin receptor ligands, Bioorganic & Medicinal Chemistry Letter (2004), 14:4697-4699.

Savola et al., Cardiovascular and Sedative α-Adrenoceptor Effects of Detomidine-like Arylalkyl Imidazoles and Associated Derivatives, Drug Res. (1988), 38:29-35.

Timmermans et al., Characterization of α-Adrenoceptor Populations. Quantitive Relationships between Cardiovascular Effects Initiated at Central and Peripheral α-Adrenoceptors, J. Med. Chem. (1981), 24:502-507.

Timmermans et al., Correlations between Central Hypotensive and Peripheral Hypertensive Effects of Structurally Dissimilar Alpha-Adrenoceptor Agonists, Life Sciences (1981), 28:653-660.

Turner et al., A Facile Route to Imidazol-4-yl Anions and Their Reaction with Carbonyl Compounds, J. Org. Chem. (1991), 56: 5739-5740.

Freiter, E.R., et al., J. Heterocyclic Chem., vol. 10, No. 3, pp. 391-394 (1973), XP008087527.

Tarnchompoo, B., et al., vol. 31, No. 40, pp. 5779-5780 (1990), XP002118267, Tetrahedron Letters.

Wilkinson, C.F., et al., Biochem. Pharmacol., vol. 21, pp. 3187-3192 (1972), XP :008087536.

Raddatz, Rita , et al., J. Pharmacol. Exp. Therap., vol. 292, No. 3, pp. 1135-1145 (2000), XP008087488.

Shafiee, A., et al., Journal of Heterocyclic Chemistry, pp. 607-610 (1998), XP001069546.

Robertson, David W., J. Med. Chem., vol. 29, pp. 1577-1586 (1986), XP008087539.

Yu M et al, *Organic Letters*, 7(17):3677-3680 (2005).

Ranganathan D et al, Tetrahedron Letters, 25(49):5701-5704 (1984).

Ho B et al, *J. of Pharma Sciences*, 58(5):563-566 (1969).

Petricci E et al, *Tetrahedron Letters*, 43(37):6507-6509 (2002).

Chen et al, *Chemical Abstract* 2007:462041, XP002499911.

\* cited by examiner

TAAR1 LIGANDS

PRIORITY TO RELATED APPLICATION(S)

This application claims the benefit of European Patent Application No. 07113752.5, filed Aug. 3, 2007, which is hereby incorporated by reference in its entirety.

BACKGROUND OF THE INVENTION

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "cross reacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors.

REFERENCES USED

1 Deutch, A. Y. and Roth, R. H. (1999) Neurotransmitters. In *Fundamental Neuroscience* (2$^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol. 1: Trace Amines and the Brain.* [Proceedings of a Study Group at the 14th Annual Meeting of the American College of Neuropsychoparmacology, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

SUMMARY OF THE INVENTION

The invention provides a compound of formula

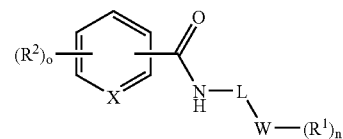

wherein
$R^1$ is hydrogen, halogen, lower alkyl, lower alkoxy, lower alkyl substituted by halogen, —O—$(CH_2)_p$-aryl or aryl;
$R^2$ is halogen, lower alkyl substituted by halogen, NR'R", —$(CH_2)_p$-heteroaryl or is —O-heterocycloalkyl, wherein the substitution on heteroaryl or heterocycloalkyl is lower alkyl;
R' and R" are each independently hydrogen, —$(CH_2)_p$—O-lower alkyl,
—$(CH_2)_p$-optionally substituted aryl, —$(CH_2)_p$-heteroaryl, —$(CH_2)_p$-heterocycloalkyl, or R' and R" together with the N atom to which they are attached form a heterocycloalkyl group optionally substituted by lower alkyl, —CH$_2$-cycloalkyl, —S(O)$_2$CH$_3$, —(CH$_2$)$_p$—O-lower alkyl or by substituted aryl wherein the substitution on aryl is lower alkyl or lower alkoxy;

W is phenyl, benzo[1,3]dioxolyl, pyridine-2,3- or 4-yl, indolyl or cycloalkyl;

L is —CH$_2$—, —CH(CH$_3$)—, —CH$_2$CH$_2$—, —CH$_2$CH(CH$_3$)— or —CH$_2$CH$_2$CH$_2$—;

X is N or CH;

n is 1 or 2; in case n is 2, each R$^1$ can be the same or different;

o is 1 or 2; in case o is 2, each R$^2$ can be the same or different; and p is 0, 1, 2 or 3, or to a pharmaceutically suitable acid addition salt thereof, with the exception of the following compounds 6-(4-methyl-piperazin-1-yl)-N-phenethyl-nicotinamide (CAS 199478-31-4), N-(3,4-dichloro-benzyl)-3-fluoro-benzamide (CAS 424815-98-5), N-(4-chloro-benzyl)-3-fluoro-benzamide (CAS 544661-83-8), N-(3-chloro-benzyl)-3-fluoro-benzamide (CAS 796051-07-5), and N-phenethyl-6-phenylamino-nicotinamide (CAS 571913-74-1).

The invention includes all racemic mixtures, all their corresponding enantiomers and/or optical isomers.

The present invention also provides pharmaceutical compositions containing a compound of formula I or a pharmaceutically acceptable acid addition salt thereof and a pharmaceutically acceptable carrier. The invention further provides methods for the manufacture of the compounds and compositions of the present invention.

Compounds of formula I have a good affinity to the trace amine associated receptors (TAARs), especially for TAAR1.

The compounds are useful for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety and attention deficit hyperactivity disorder (ADHD).

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes an alkyl group as defined above, which is attached via an oxygen atom.

As used herein, the term "lower alkyl substituted by halogen" denotes an alkyl group as defined above, wherein at least one hydrogen atom is replaced by halogen, for example CF$_3$, CHF$_2$, CH$_2$F, CH$_2$CF$_3$, CH$_2$CH$_2$CF$_3$, CH$_2$CF$_2$CF$_3$ and the like.

The term "halogen" denotes chlorine, iodine, fluorine and bromine.

The term "cycloalkyl" denotes a saturated carbocyclic ring, containing from 3 to 6 carbon atoms, for example, cyclopropyl, cyclobutyl, cyclopentyl or cyclohexyl.

The term "aryl" as used herein is a carbocyclic ring system, containing from 6 to 10 carbon atoms forming one or more rings, and wherein at least one ring is aromatic in nature, for example phenyl, naphthyl or 5,6,7,8-tetrahydronaphthalen-1-yl. The most preferred aryl group is phenyl.

The term "heteroaryl" as used herein is an aromatic ring system, containing from 5 to 10 ring atoms forming one or more rings, wherein at least one ring atom is a heteroatom selected from the group consisting of O, N and S, and wherein at least one ring is aromatic in nature, for example oxazolyl, pyridyl, thiophenyl, quinolinyl, pyrrolyl, furyl, benzoimidazolyl, imidazolyl and the like. The most preferred group is pyridyl.

The term heterocycloalkyl denotes a fully saturated ring system, wherein one or two ring atoms are N, O or S, for example piperazinyl, pyrrolidinyl, morpholinyl or piperidinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of formula I are those, wherein X is N. Most preferred are compounds of formula

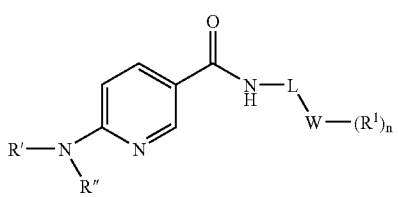

IA wherein

R$^1$ is hydrogen, halogen, lower alkyl, lower alkoxy, lower alkyl substituted by halogen, —O—(CH$_2$)$_p$-aryl or aryl;

R' and R" are each independently hydrogen, —(CH$_2$)$_p$—O-lower alkyl,
—(CH$_2$)$_p$-optionally substituted aryl, —(CH$_2$)$_p$-heteroaryl, —(CH$_2$)$_p$-heterocycloalkyl, or R' and R" together with the N atom to which they are attached form a heterocycloalkyl group optionally substituted by lower alkyl, —CH$_2$-cycloalkyl, —S(O)$_2$CH$_3$, —(CH$_2$)$_p$—O-lower alkyl or by substituted aryl wherein the substitution on aryl is lower alkyl or lower alkoxy W is phenyl, benzo[1,3]dioxolyl, pyridine-2,3- or 4-yl, indolyl or cycloalkyl;

L is —CH$_2$—, —CH(CH$_3$)—, —CH$_2$CH$_2$—, —CH$_2$CH(CH$_3$)—, —CH$_2$CH$_2$CH$_2$—, n is 1 or 2; in case n is 2, each R$^1$ can be the same or different;

p is 0, 1, 2 or 3;

or a pharmaceutically suitable acid addition salt thereof, with the exception of the following compounds 6-(4-methyl-piperazin-1-yl)-N-phenethyl-nicotinamide (CAS 199478-31-4) and N-phenethyl-6-phenylamino-nicotinamide (CAS 571913-74-1).

Preferred compounds from this group are those, wherein —NR'R'' together form a heterocycloalkyl group, more specifically 4-methyl-piperazin-1-yl, for example the following compounds N-benzyl-6-(4-methyl-piperazin-1-yl)-nicotinamide, (N-(4-chloro-benzyl)-6-(4-methyl-piperazin-1-yl)-nicotinamide, N-[2-(4-chloro-phenyl)-ethyl]-6-(4-methyl-piperazin-1-yl)-nicotinamide, N-[2-(3-chloro-phenyl)-ethyl]-6-(4-methyl-piperazin-1-yl)-nicotinamide, 6-(4-methyl-piperazin-1-yl)-N-[2-(3-trifluoromethyl-phenyl)-ethyl]-nicotinamide, N-[2-(4-methoxy-phenyl)-ethyl]-6-(4-methyl-piperazin-1-yl)-nicotinamide, N-[2-(3-methoxy-phenyl)-ethyl]-6-(4-methyl-piperazin-1-yl)-nicotinamide, N-(2-benzo[1,3]dioxol-5-yl-ethyl)-6-(4-methyl-piperazin-1-yl)-nicotinamide, N-(2-biphenyl-4-yl-ethyl)-6-(4-methyl-piperazin-1-yl)-nicotinamide, 6-(4-methyl-piperazin-1-yl)-N-[2-(4-phenoxy-phenyl)-ethyl]-nicotinamide, 6-(4-methyl-piperazin-1-yl)-N-[2-(3-phenoxy-phenyl)-ethyl]-nicotinamide, N-[2-(4-benzyloxy-phenyl)-ethyl]-6-(4-methyl-piperazin-1-yl)-nicotinamide, N-[2-(1-methyl-1H-indol-3-yl)-ethyl]-6-(4-methyl-piperazin-1-yl)-nicotinamide, N-(2-cyclohexyl-ethyl)-6-(4-methyl-piperazin-1-yl)-nicotinamide, or N-cyclohexylmethyl-6-(4-methyl-piperazin-1-yl)-nicotinamide.

Preferred compounds from this group are further those, wherein —NR'R'' form together a heterocycloalkyl group, for example piperazin-1-yl, such as N-[2-(4-chloro-phenyl)-ethyl]-6-piperazin-1-yl-nicotinamide, N-[2-(4-phenoxy-phenyl)-ethyl]-6-piperazin-1-yl-nicotinamide, N-[2-(3-phenoxy-phenyl)-ethyl]-6-piperazin-1-yl-nicotinamide, or N-[2-(4-benzyloxy-phenyl)-ethyl]-6-piperazin-1-yl-nicotinamide.

Further preferred are compounds, wherein R$^2$ is —O-heterocycloalkyl, more specifically 1-methyl-piperidin-4-yloxy, for example the following compound 6-(1-Methyl-piperidin-4-yloxy)-N-[2-(4-phenoxy-phenyl)-ethyl]-nicotinamide.

Preferred compounds from this group are those, wherein o is 2 and one of R$^2$ is NR'R'' and the other R$^2$ is halogen, for example the following compounds 5-bromo-N-[2-(4-chloro-phenyl)-ethyl]-6-(4-methyl-piperazin-1-yl)-nicotinamide, 5-bromo-6-(4-methyl-piperazin-1-yl)-N-[2-(4-phenoxy-phenyl)-ethyl]-nicotinamide, 5-bromo-N-[2-(4-chloro-phenyl)-ethyl]-6-piperazin-1-yl-nicotinamide, or 5-bromo-N-[2-(4-phenoxy-phenyl)-ethyl]-6-piperazin-1-yl-nicotinamide.

One embodiment of the invention are compounds of formula I,

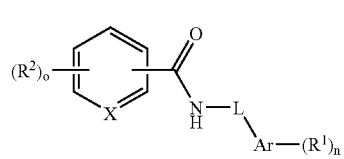

wherein

R$^1$ is hydrogen, halogen, lower alkyl, lower alkoxy, lower alkyl substituted by halogen, —O—(CH$_2$)$_p$-aryl or aryl;

R$^2$ is halogen, lower alkyl substituted by halogen, NR'R'', —(CH$_2$)$_p$-heteroaryl or —O-heterocycloalkyl, wherein the substitution on heteroaryl or heterocycloalkyl is lower alkyl;

R' and R'' are each independently hydrogen, —(CH$_2$)$_p$—O-lower alkyl,

—(CH$_2$)$_p$-optionally substituted aryl, —(CH$_2$)$_p$-heteroaryl, —(CH$_2$)$_p$-heterocycloalkyl, or R' and R'' together with the N atom to which they are attached form a heterocycloalkyl group optionally substituted by lower alkyl, —CH$_2$-cycloalkyl, —S(O)$_2$CH$_3$, —(CH$_2$)$_p$—O-lower alkyl or by substituted aryl wherein the substitution on aryl is lower alkyl or lower alkoxy;

Ar is phenyl, benzo[1,3]dioxolyl, pyridine-2,3- or 4-yl or is indolyl;

L is —CH$_2$—, —CH(CH$_3$)—, —CH$_2$CH$_2$—, —CH$_2$CH(CH$_3$)— or —CH$_2$CH$_2$CH$_2$—;

X is N or CH;

n is 1 or 2; in case n is 2, each R$^1$ can be the same or different;

o is 1 or 2; in case o is 2, each R$^2$ can be the same or different;

p is 0, 1, 2 or 3;

or a pharmaceutically suitable acid addition salt thereof, with the exception of the following compounds 6-(4-methyl-piperazin-1-yl)-N-phenethyl-nicotinamide, N-(3,4-dichloro-benzyl)-3-fluoro-benzamide, N-(4-chloro-benzyl)-3-fluoro-benzamide, N-(3-chloro-benzyl)-3-fluoro-benzamide, and N-phenethyl-6-phenylamino-nicotinamide.

The present compounds of formula I and their pharmaceutically acceptable salts can be prepared by methods known in the art, for example, by processes described below, which processes comprise a) reacting a compound of formula

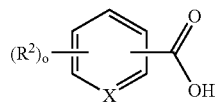

II with an amine of formula

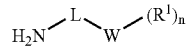

III to give a compound of formula

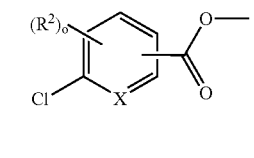

I wherein the definitions are as described above, or if desired, converting the compounds obtained into pharmaceutically acceptable acid addition salts.

The compounds of formula I can be prepared in accordance with the process variants as described above and with the following schemes 1 and 2. The starting materials are either commercially available, are otherwise known in the chemical literature, or can be prepared in accordance with methods well known in the art.

General Procedure

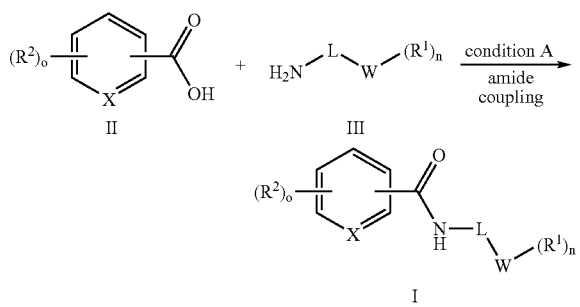

The definition of substituents is as described above.

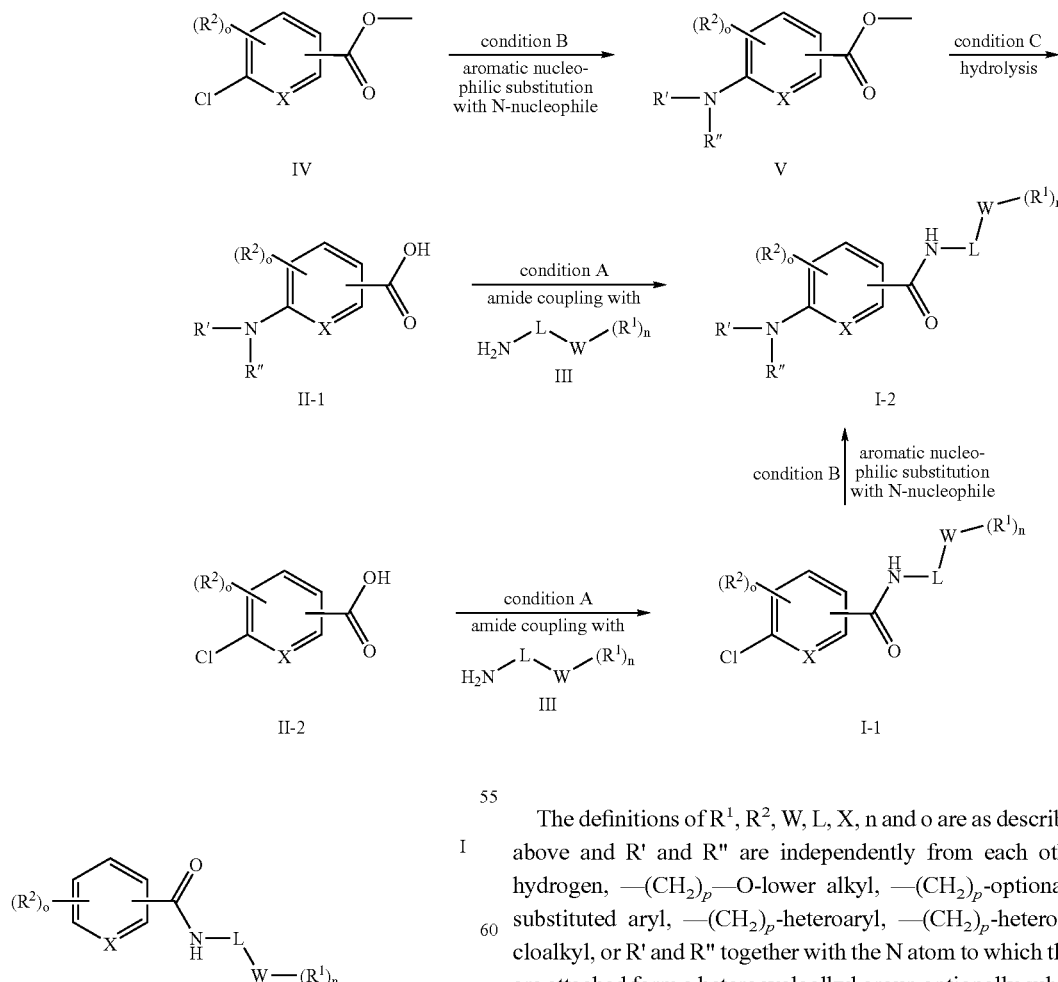

The definitions of $R^1$, $R^2$, W, L, X, n and o are as described above and R' and R" are independently from each other hydrogen, —$(CH_2)_p$—O-lower alkyl, —$(CH_2)_p$-optionally substituted aryl, —$(CH_2)_p$-heteroaryl, —$(CH_2)_p$-heterocycloalkyl, or R' and R" together with the N atom to which they are attached form a heterocycloalkyl group optionally substituted by lower alkyl, —$CH_2$-cycloalkyl, —$S(O)_2CH_3$, —$(CH_2)_p$—O-lower alkyl or by substituted aryl, wherein the substitution on aryl is lower alkyl or lower alkoxy and wherein p has the definition as described below.

Scheme 3

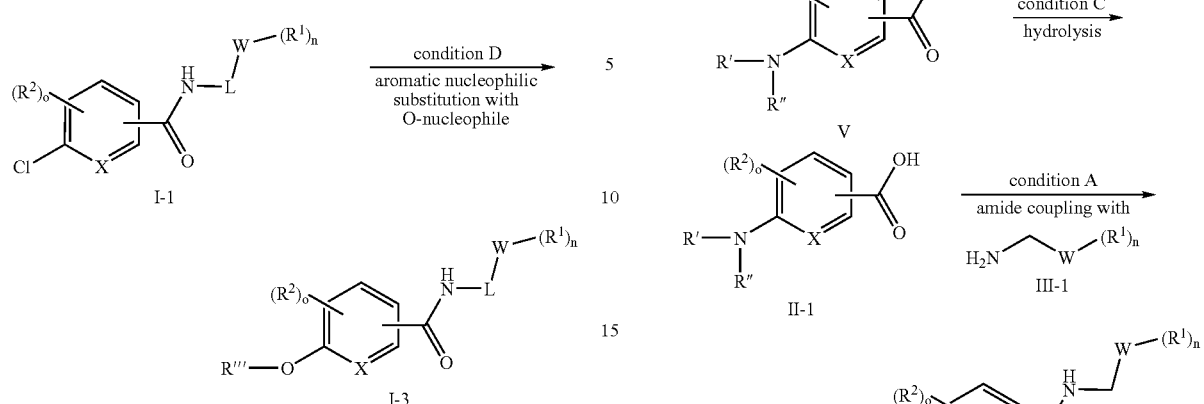

The definitions of $R^1$, $R^2$, X, L, W, n and o are as described above and R''' is a heterocycloalkyl group, optionally substituted by lower alkyl.

Scheme 4

The definitions of $R^1$, $R^2$, W, L, X, n and o are as described above and R' and R'' are independently from each other hydrogen, —$(CH_2)_p$—O-lower alkyl, —$(CH_2)_p$-optionally substituted aryl, —$(CH_2)_p$-heteroaryl, —$(CH_2)_p$-heterocycloalkyl, or R' and R'' together with the N atom to which they are attached form a heterocycloalkyl group optionally substituted by lower alkyl, —$CH_2$-cycloalkyl, —$S(O)_2CH_3$, —$(CH_2)_p$—O-lower alkyl or by substituted aryl, wherein the substitution on aryl is lower alkyl or lower alkoxy, wherein p has the definition as described below.

Scheme 5

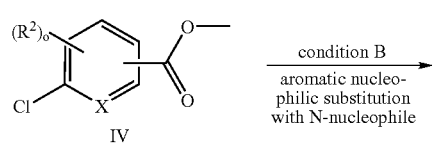

The definitions of $R^1$, $R^2$, W, X, n and o are as described above and R' and R'' are independently from each other hydrogen, —$(CH_2)_p$—O-lower alkyl, —$(CH_2)_p$-optionally substituted aryl, —$(CH_2)_p$-heteroaryl, —$(CH_2)_p$-heterocycloalkyl, or R' and R'' together with the N atom to which they are attached form a heterocycloalkyl group optionally substituted by lower alkyl, —$CH_2$-cycloalkyl, —$S(O)_2CH_3$, —$(CH_2)_p$—O-lower alkyl or by substituted aryl, wherein the substitution on aryl is lower alkyl or lower alkoxy, wherein p has the definition as described below.

Condition A: Amide couplings are carried out in a solvent such as $CH_2Cl_2$, DMF, acetonitrile, THF or mixtures thereof. Activation is effected by an amide coupling reagent such as BOP, BOP-Cl, TBTU, EDCI, EDCI/DMAP and an additive such as HOBT, N-hydroxysuccinimide or N-hydroxy-2-pyridone in the presence of a base like TEA, DIPEA, N-methylmorpholine etc. at 0° C. to 100° C. Reaction times ranged from 1 hr to 72 hrs.

Preferred conditions are DMF, BOP and DIPEA at r.t. overnight.

Step B: Nucleophilic substitution of chloronicotinic acid derivatives by a suitable primary or secondary amine is carried out in a solvent such as DMF in the presence of a base such as TEA, DIPEA, N-methylmorpholine at 50° C. to reflux. Reaction times range from 2 hrs to 72 hrs.

Preferred conditions are DMF, DIPEA at 80° C. for 5 hrs.

Condition C: Ester hydrolysis is effected by dissolving it in a suitable solvent like MeOH, EtOH, THF, 1,4-dioxane, water or mixtures thereof and a base like LiOH, NaOH, KOH, $Na_2CO_3$, $K_2CO_3$ or $Cs_2CO_3$.

Preferred conditions are NaOH in EtOH/$H_2O$.

Condition D: Nucleophilic substitution of chloronicotinic acid derivatives by a suitable alcohol is carried out in a solvent such as DMSO in the presence of a base such as KOH at 100° C. in the microwave oven. Reaction times range from 5 min to 30 min.

Condition E: Boc cleavage is effected by treatment with a mineral acid such as HCl, HBr, $H_2SO_4$ or $H_3PO_4$ or a carbonic acid, in a solvent such as $CH_2Cl_2$, dioxane or HOAc at 0 to 60° C.

Preferred conditions are 4N HCl in dioxane at r.t. overnight.
The following abbreviations have been used:
DMF=N,N-dimethylformamide
BOP=benzotriazol-1-yloxy-tri(dimethyl-amino)phosphonium hexafluorophosphate
EDCI=1-(3-dimethylaminopropyl)-3-ethylcarbodiimide hydrochloride
DMAP=4-dimethylaminopyridine
HOBT=1-hydroxybenzotriazole hydrate
THF=tetrahydrofurane
DMSO=methyl sulfoxide Isolation and Purification of the Compounds Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM $Mg^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Membrane Preparation and Radioligand Binding

Cells at confluence were rinsed with ice-cold phosphate buffered saline without $Ca^{2+}$ and $Mg^{2+}$ containing 10 mM EDTA and pelleted by centrifugation at 1000 rpm for 5 min at 4° C. The pellet was then washed twice with ice-cold phosphate buffered saline and cell pellet was frozen immediately by immersion in liquid nitrogen and stored until use at −80° C. Cell pellet was then suspended in 20 ml HEPES-NaOH (20 mM), pH 7.4 containing 10 mM EDTA, and homogenized with a Polytron (PT 3000, Kinematica) at 10,000 rpm for 10 s. The homogenate was centrifuged at 48,000×g for 30 min at 4° C. and the pellet resuspended in 20 ml HEPES-NaOH (20 mM), pH 7.4 containing 0.1 mM EDTA (buffer A), and homogenized with a Polytron at 10,000 rpm for 10 s. The homogenate was then centrifuged at 48,000×g for 30 min at 4° C. and the pellet resuspended in 20 ml buffer A, and homogenized with a Polytron at 10,000 rpm for 10 s. Protein concentration was determined by the method of Pierce (Rockford, Ill.). The homogenate was then centrifuged at 48,000×g for 10 min at 4° C., resuspended in HEPES-NaOH (20 mM), pH 7.0 including $MgCl_2$ (10 mM) and $CaCl_2$ g protein per ml and (2 mM) (buffer B) at 200 homogenized with a Polytron at 10,000 rpm for 10 s.

Binding assay was performed at 4° C. in a final volume of 1 ml, and with an incubation time of 30 min. The radioligand [$^3$H]-rac-2-(1,2,3,4-tetrahydro-1-naphthyl)-2-imidazoline was used at a concentration equal to the calculated $K_d$ value of 60 nM to give a bound at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 μM). Competing ligands were tested in a wide range of concentrations (10 pM-30 μM). The final dimethylsulphoxide concentration in the assay was 2%, and it did not affect radioligand binding. Each experiment was performed in duplicate. All incubations were terminated by rapid filtration through UniFilter-96 plates (Packard Instrument Company) and glass filter GF/C, pre-soaked for at least 2 h in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 μl/well, Packard Instrument Company) and bound radioactivity was counted by a TopCount Microplate Scintillation Counter (Packard Instrument Company).

The preferred compounds show a Ki value (μM) in mouse on TAAR1 in the range of <0.1 μM. Values for representative compounds are shown in the table below.

| Example | Ki (μM) mouse |
|---|---|
| 1 | 0.071 |
| 2 | 0.013 |
| 6 | 0.005 |
| 7 | 0.027 |
| 8 | 0.010 |
| 9 | 0.091 |
| 10 | 0.049 |
| 11 | 0.043 |
| 12 | 0.028 |
| 13 | 0.004 |
| 14 | 0.068 |
| 15 | 0.006 |
| 18 | 0.023 |
| 24 | 0.019 |
| 26 | 0.081 |
| 28 | 0.016 |
| 29 | 0.071 |
| 30 | 0.028 |
| 31 | 0.006 |
| 32 | 0.005 |
| 33 | 0.019 |
| 34 | 0.009 |
| 54 | 0.012 |
| 55 | 0.062 |
| A | 0.044 |

The present invention also provides pharmaceutical compositions containing compounds of the invention, for example compounds of formula (I) and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment or prevention of depression, psychosis, Parkinson's disease, anxiety and attention deficit hyperactivity disorder (ADHD).

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| | Tablet Formulation (Wet Granulation) | | | | |
|---|---|---|---|---|---|
| | | mg/tablet | | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | Capsule Formulation | | | | |
|---|---|---|---|---|---|
| | | mg/capsule | | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXPERIMENTAL

The following examples illustrate the invention but are not intended to limit its scope.

Example 1

N-Benzyl-6-(4-methyl-piperazin-1-yl)-nicotinamide a) 6-(4-Methyl-piperazin-1-yl)-nicotinic acid methyl ester

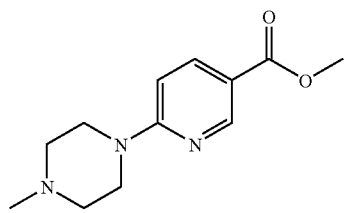

Methyl 6-chloronicotinate (5.0 g) was dissolved in DMF (75 ml) at r.t. under an argon atmosphere. 1-Methylpiperazine (3.66 ml) and diisopropylethylamine (30.7 ml) were added and the solution was stirred for 5 hours at 80° C. The reaction was quenched with water. The solution was extracted with EtOAc. The water phase was twice washed with EtOAc. The combined organic layers were washed with water and sat. aq. NaCl, dried over MgSO$_4$, filtered and concentrated. The crude product was purified by column chromatography (silica gel; gradient: CH$_2$Cl$_2$→CH$_2$Cl$_2$/MeOH 9:1) to give 6-(4-methyl-piperazin-1-yl)-nicotinic acid methyl ester (5.59 g) as light yellow solid.

MS (ISP): 236.1 ([M+H]$^+$).

b) 6-(4-Methyl-piperazin-1-yl)-nicotinic acid

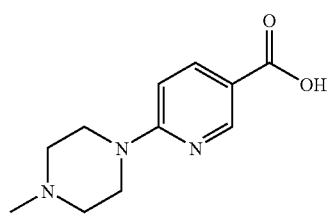

A solution of 6-(4-methyl-piperazin-1-yl)-nicotinic acid methyl ester (5.56 g) in MeOH/H$_2$O 1:1 (100 ml) was cooled to 0° C. and treated with NaOH (1.9 g). The reaction mixture was stirred for 45 min at 0° C. and for 5 hrs at r.t., then neutralized with 1N HCl and concentrated. The crude product was used in the next reaction step without further purification.

MS (ISP): 220.6 ([M−H])

c) N-Benzyl-6-(4-methyl-piperazin-1-yl)-nicotinamide

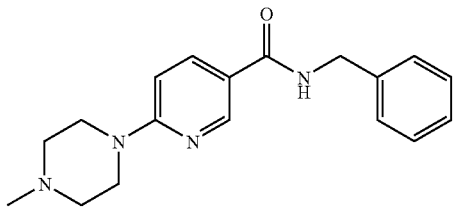

A suspension of 6-(4-methyl-piperazin-1-yl)-nicotinic acid (200 mg) in DMF (2 ml) was treated under an argon atmosphere with diisopropylamine (0.50 ml), benzylamine (0.12 ml) and BOP (600 mg). The reaction mixture was stirred at r.t. overnight, then diluted with water and extracted with EtOAc. The combined organic layers were washed with water and brine, dried over MgSO$_4$, filtered and concentrated. The crude product was purified by column chromatography (silica gel; gradient: CH$_2$Cl$_2$→CH$_2$Cl$_2$/MeOH 9:1) to give N-benzyl-6-(4-methyl-piperazin-1-yl)-nicotinamide (120 mg) as off-white solid. MS (ISP): 311.3 ([M+H]$^+$)

In analogy to example 1c using the appropriate amine component were prepared:

Example 2

(N-(4-Chloro-benzyl)-6-(4-methyl-piperazin-1-yl)-nicotinamide

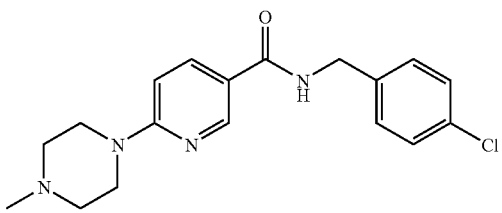

Amine: 4-chlorobenzylamine. Off-white solid. MS (ISP): 345.1 ([M+H]$^+$)

Example 3

6-(4-Methyl-piperazin-1-yl)-N-(4-phenoxy-benzyl)-nicotinamide

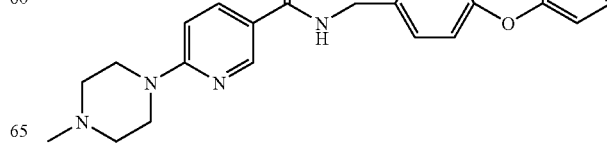

Amine: 4-phenoxybenzylamine. White solid. MS (ISP): 403.5 ([M+H]+)

Example 4

N-Benzyl-6-piperazin-1-yl-nicotinamide a) 4-(5-Benzylcarbamoyl-pyridin-2-yl)-piperazine-1-carboxylic acid tert-butyl ester

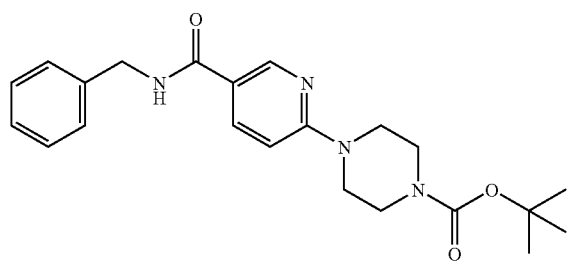

In analogy to example 1 4-(5-phenethylcarbamoyl-pyridin-2-yl)-piperazine-1-carboxylic acid tert-butyl ester was prepared starting from N-Boc-piperazine and using benzylamine in the last coupling step. Light yellow solid. MS (ISP): 397.5 ([M+H]+)

b) N-Benzyl-6-piperazin-1-yl-nicotinamide

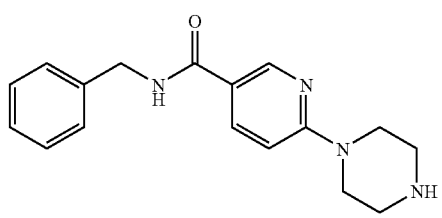

A solution of 4-(5-phenethylcarbamoyl-pyridin-2-yl)-piperazine-1-carboxylic acid tert-butyl ester (200 mg) in MeOH (5 ml) was cooled to 0° C. and slowly treated with 4N HCl (2.52 ml). The reaction mixture was stirred at r.t. overnight, then diluted with $CH_2Cl_2$ and directly purified by column chromatography (Isolute® SPE flash $NH_2$ column, aminopropyl-functionalized silica; gradient: $CH_2Cl_2 \rightarrow CH_2Cl_2/$ MeOH 9:1) to give N-benzyl-6-piperazin-1-yl-nicotinamide as off-white solid. MS (ISP): 297.5 ([M+H]+)

In analogy to example 1c using the appropriate amine component were prepared:

Example 5

(RS)-6-(4-Methyl-piperazin-1-yl)-N-(2-phenyl-propyl)-nicotinamide

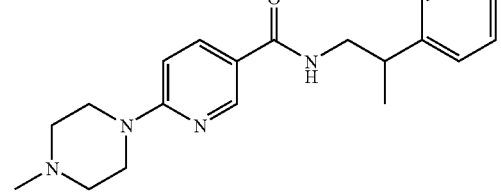

Amine: 2-methylphenylethylamine. White solid. MS (ISP): 339.3 ([M+H]+)

Example 6

N-[2-(4-Chloro-phenyl)-ethyl]-6-(4-methyl-piperazin-1-yl)-nicotinamide

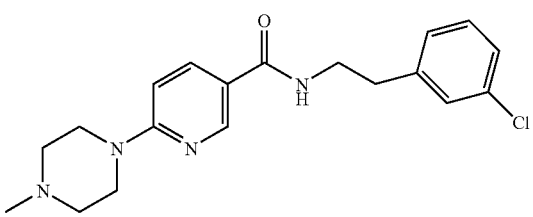

Amine: 2-(4-chlorophenyl)ethylamine. White solid. MS (ISP): 359.1 ([M+H]+)

Example 7

N-[2-(3-Chloro-phenyl)-ethyl]-6-(4-methyl-piperazin-1-yl)-nicotinamide

Amine: 2-(3-chlorophenyl)ethylamine. White solid. MS (ISP): 359.1 ([M+H]+)

Example 8

6-(4-Methyl-piperazin-1-yl)-N-[2-(3-trifluoromethyl-phenyl)-ethyl]-nicotinamide

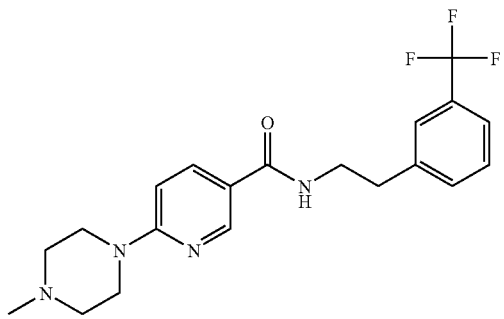

Amine: 2-(3-trifluoromethylphenyl)ethylamine. White solid. MS (ISP): 393.3 ([M+H]+)

Example 9

N-[2-(4-Methoxy-phenyl)-ethyl]-6-(4-methyl-piperazin-1-yl)-nicotinamide

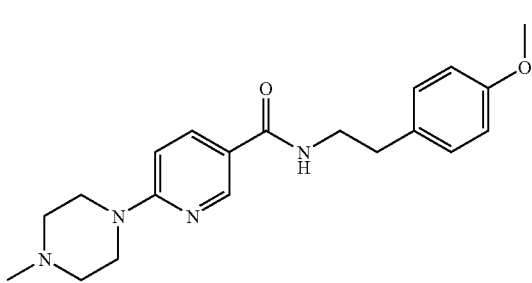

Amine: 2-(4-methoxyphenyl)ethylamine. Off-white solid. MS (ISP): 355.4 ([M+H]+)

Example 10

N-[2-(3-Methoxy-phenyl)-ethyl]-6-(4-methyl-piperazin-1-yl)-nicotinamide

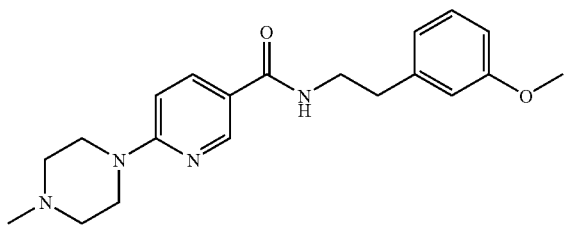

Amine: 2-(3-methoxyphenyl)ethylamine. Colorless oil. MS (ISP): 355.4 ([M+H]+)

Example 11

N-(2-Benzo[1,3]dioxol-5-yl-ethyl)-6-(4-methyl-piperazin-1-yl)-nicotinamide

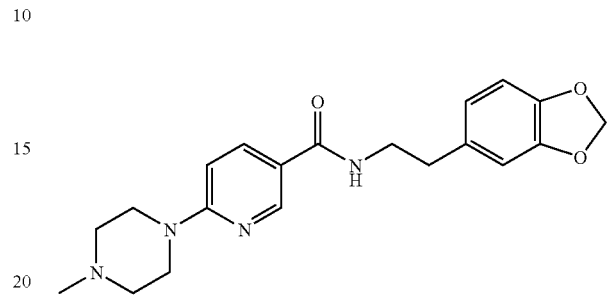

Amine: 3,4-methylenedioxyphenethylamine hydrochloride. White solid. MS (ISP): 369.4 ([M+H]+)

Example 12

N-(2-Biphenyl-4-yl-ethyl)-6-(4-methyl-piperazin-1-yl)-nicotinamide

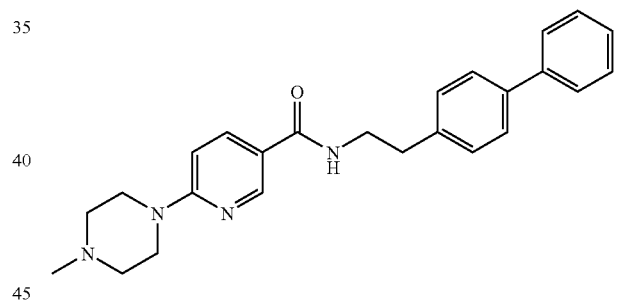

Amine: 2-(4-biphenyl)ethylamine. White solid. MS (ISP): 401.5 ([M+H]+)

Example 13

6-(4-Methyl-piperazin-1-yl)-N-[2-(4-phenoxy-phenyl)-ethyl]-nicotinamide

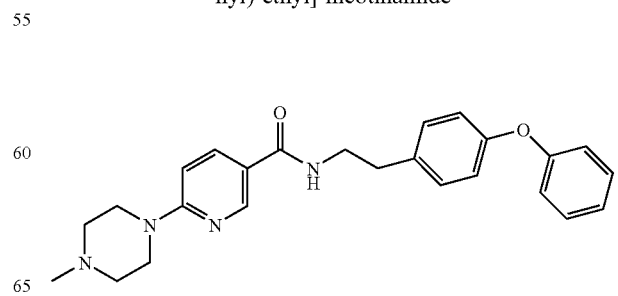

Amine: 4-phenoxyphenetylamine. Off-white solid. MS (ISP): 417.4 ([M+H]⁺)

Example 14

6-(4-Methyl-piperazin-1-yl)-N-[2-(3-phenoxy-phenyl)-ethyl]-nicotinamide

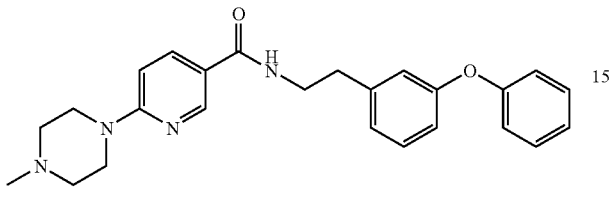

Amine: 3-phenoxyphenethylamine. Off-white solid. MS (ISP): 417.4 ([M+H]⁺)

Example 15

N-[2-(4-Benzyloxy-phenyl)-ethyl]-6-(4-methyl-piperazin-1-yl)-nicotinamide

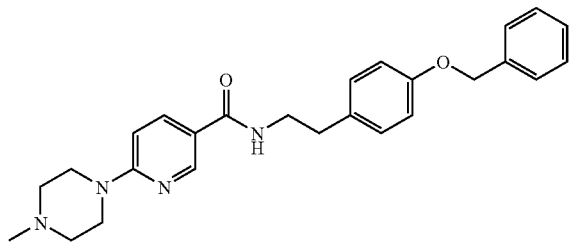

Amine: 2-(4-benzyloxy-phenyl)-ethylamine. Off-white solid. MS (ISP): 431.5 ([M+H]⁺)

Example 16

6-(4-Methyl-piperazin-1-yl)-N-(2-pyridin-2-yl-ethyl)-nicotinamide

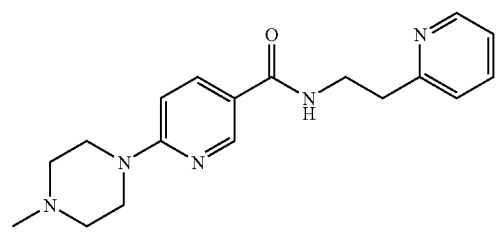

Amine: 2-(2-aminoethyl)pyridine. Light yellow solid. MS (ISP): 326.5 ([M+H]⁺)

Example 17

6-(4-Methyl-piperazin-1-yl)-N-(2-pyridin-3-yl-ethyl)-nicotinamide

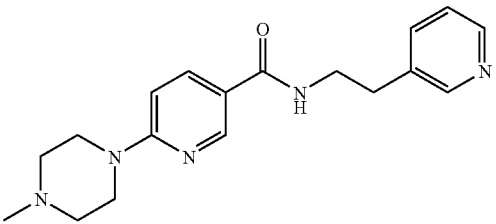

Amine: 3-(2-aminoethyl)pyridine. Light yellow solid. MS (ISP): 326.3 ([M+H]⁺)

Example 18

N-[2-(1-Methyl-1H-indol-3-yl)-ethyl]-6-(4-methyl-piperazin-1-yl)-nicotinamide

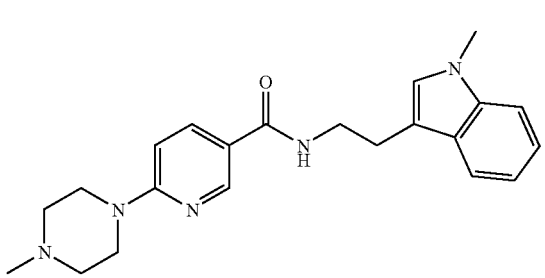

Amine: 1-methyltryptamine. Off-white liquid. MS (ISP): 378.4 ([M+H]⁺)

Example 19

N-[2-(1H-Indol-3-yl)-ethyl]-6-(4-methyl-piperazin-1-yl)-nicotinamide

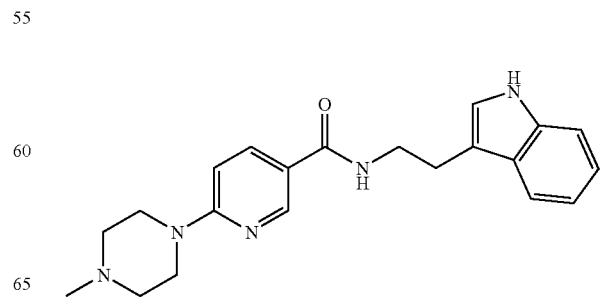

Amine: tryptamine. Off-white solid. MS (ISP): 364.3 ([M+H]+)

Example 20

N-[2-(4-Chloro-phenyl)-ethyl]-6-(4-cyclopropylmethyl-piperazin-1-yl)-nicotinamide a) 6-Chloro-N-[2-(4-chloro-phenyl)-ethyl]-nicotinamide

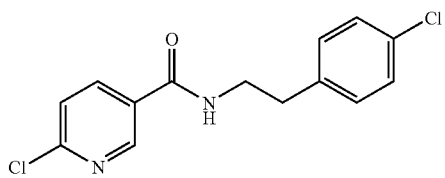

In analogy to example 1.c 6-chloro-nicotinic acid was coupled with 2-(4-chlorophenyl)ethylamine. Light yellow solid. MS (ISP): 294.0 ([M+H]+)

b) N-[2-(4-Chloro-phenyl)-ethyl]-6-(4-cyclopropyl-methyl-piperazin-1-yl)-nicotinamide

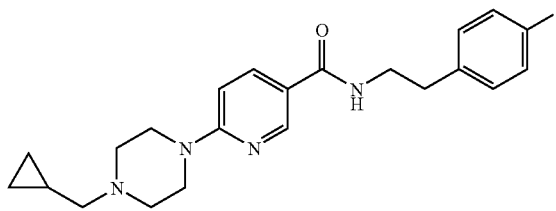

In analogy to example 1.a 6-chloro-N-[2-(4-chloro-phenyl)-ethyl]-nicotinamide was reacted with 1-(cyclopropylmethyl)piperazine. Off-white solid. MS (ISP): 399.3 ([M+H]+)

Example 21

N-[2-(4-Chloro-phenyl)-ethyl]-6-[4-(2-methoxy-ethyl)-piperazin-1-yl]-nicotinamide

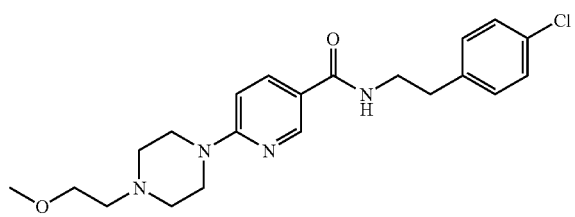

In analogy to example 21.b 6-chloro-N-[2-(4-chloro-phenyl)-ethyl]-nicotinamide was reacted with 1-(2-methoxyethyl)piperazine. Light yellow solid. MS (ISP): 403.3 ([M+H]+)

Example 22

N-[2-(4-Phenoxy-phenyl)-ethyl]-6-pyrrolidin-1-yl-nicotinamide

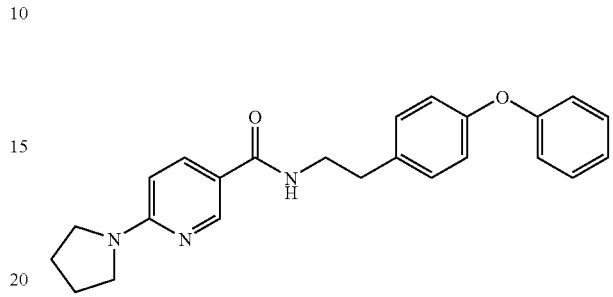

In analogy to example 21, 6-chloro-nicotinic acid was coupled with 4-phenoxyphenethylamine. The intermediate 6-chloro-N-[2-(4-phenoxy-phenyl)-ethyl]-nicotinamide was reacted with piperidine. White solid. MS (ISP): 388.3 ([M+H]+)

Example 23

6-Morpholin-4-yl-N-[2-(4-phenoxy-phenyl)-ethyl]-nicotinamide

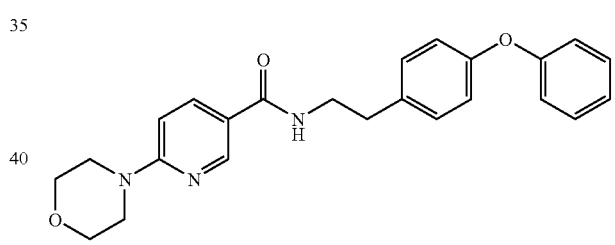

In analogy to example 21 6-chloro-nicotinic acid was coupled with 4-phenoxyphenethylamine. The intermediate 6-chloro-N-[2-(4-phenoxy-phenyl)-ethyl]-nicotinamide was reacted with morpholine. White solid. MS (ISP): 404.6 ([M+H]+)

Example 24

6-(1-Methyl-piperidin-4-yloxy)-N-[2-(4-phenoxy-phenyl)-ethyl]-nicotinamide

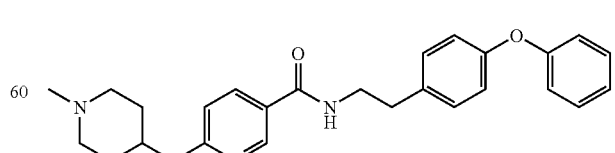

A solution of 6-chloro-N-[2-(4-phenoxy-phenyl)-ethyl]-nicotinamide (130 mg, intermediate from example 23) in DMSO (1.4 ml) was treated with 4-hydroxy-N-methylpiperidine (68 mg) and KOH (93 mg). The reaction mixture was heated for 20 min at 100° C. in the microwave oven. Then it was cooled to r.t. and diluted with CH₂Cl₂ and water. The aqueous layer was washed with CH₂Cl₂. The combined organic layers were dried over MgSO₄, filtered and concentrated. The crude product was purified by column chromatography (silica gel; gradient: CH₂Cl₂→CH₂Cl₂/MeOH 98:2) to give 6-(1-methyl-piperidin-4-yloxy)-N-[2-(4-phenoxy-phenyl)-ethyl]-nicotinamide (29 mg) as off-white solid. MS (ISP): 432.2 ([M+H]$^+$)

Example 25

N-Phenethyl-6-piperazin-1-yl-nicotinamide

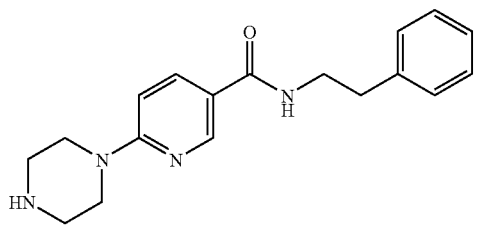

In analogy to example 4 N-phenethyl-6-piperazin-1-yl-nicotinamide was prepared starting from N-Boc-piperazine using phenethylamine in the coupling step. Off-white solid. MS (ISP): 311.4 ([M+H]$^+$)

In analogy to example 26 and using the appropriate amine in the coupling step the following derivatives were prepared:

Example 26

N-[2-(4-Chloro-phenyl)-ethyl]-6-piperazin-1-yl-nicotinamide

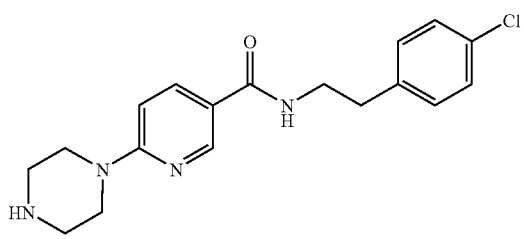

Amine: 2-(4-chlorophenyl)ethylamine. Off-white solid. MS (ISP): 345.1 ([M+H]$^+$)

Example 27

N-[2-(3-Chloro-phenyl)-ethyl]-6-piperazin-1-yl-nicotinamide

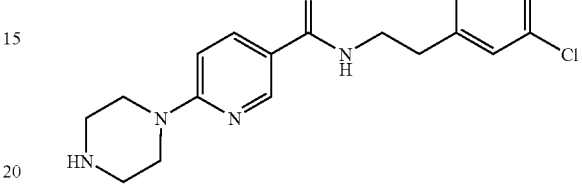

Amine: 2-(3-chlorophenyl)ethylamine. Amorphous colorless solid. MS (ISP): 345.0 ([M+H]$^+$)

Example 28

N-[2-(4-Phenoxy-phenyl)-ethyl]-6-piperazin-1-yl-nicotinamide

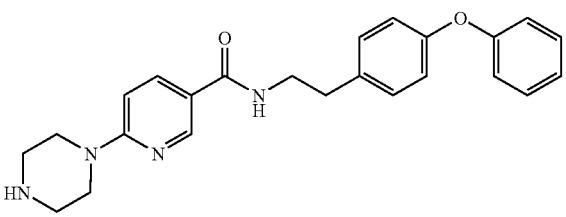

Amine: 4-phenoxyphenethylamine. Off-white solid. MS (ISP): 403.5 ([M+H]$^+$)

Example 29

N-[2-(3-Phenoxy-phenyl)-ethyl]-6-piperazin-1-yl-nicotinamide

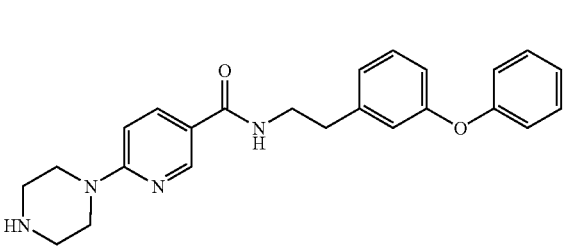

Amine: 3-phenoxyphenethylamine. Light yellow amorphous solid. MS (ISP): 403.5 ([M+H]⁺)

Example 30

N-[2-(4-Benzyloxy-phenyl)-ethyl]-6-piperazin-1-yl-nicotinamide

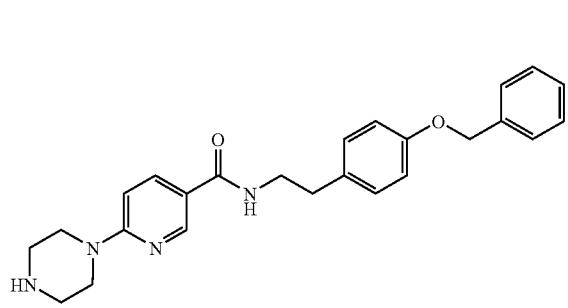

Amine: 2-(4-benzyloxy-phenyl)-ethylamine. Off-white solid. MS (ISP): 417.4 ([M+H]⁺)

Example 31

5-Bromo-N-[2-(4-chloro-phenyl)-ethyl]-6-(4-methyl-piperazin-1-yl)-nicotinamide

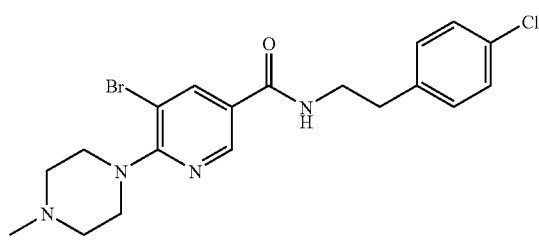

In analogy to example 1, 5-bromo-6-chloro-nicotinic acid methyl ester was reacted with N-methylpiperazine and then, using 4-chlorophenethylamine in the coupling step, converted to 5-bromo-N-[2-(4-chloro-phenyl)-ethyl]-6-(4-methyl-piperazin-1-yl)-nicotinamide. Off-white solid. MS (ISP): 437.0 ([M+H]⁺)

Example 32

5-Bromo-6-(4-methyl-piperazin-1-yl)-N-[2-(4-phenoxy-phenyl)-ethyl]-nicotinamide

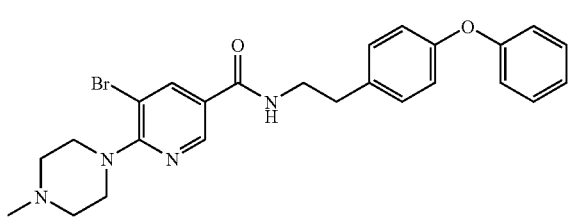

In analogy to example 32 and using 4-phenoxyphenethylamine in the coupling step 5-bromo-6-chloro-nicotinic acid methyl ester was converted to 5-bromo-6-(4-methyl-piperazin-1-yl)-N-[2-(4-phenoxy-phenyl)-ethyl]-nicotinamide. Off-white solid.
MS (ISP): 495.1 ([M+H]⁺)

Example 33

5-Bromo-N-[2-(4-chloro-phenyl)-ethyl]-6-piperazin-1-yl-nicotinamide

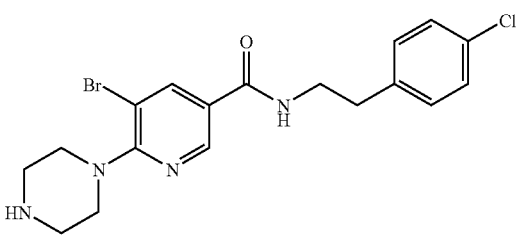

In analogy to example 26 5-bromo-6-chloro-nicotinic acid methyl ester reacted with N-Boc-piperazine and then, using 4-chlorophenethylamine in the coupling step, converted to 5-bromo-N-[2-(4-chloro-phenyl)-ethyl]-6-piperazin-1-yl-nicotinamide. Off-white solid. MS (ISP): 423.1 ([M+H]⁺)

Example 34

5-Bromo-N-[2-(4-phenoxy-phenyl)-ethyl]-6-piperazin-1-yl-nicotinamide

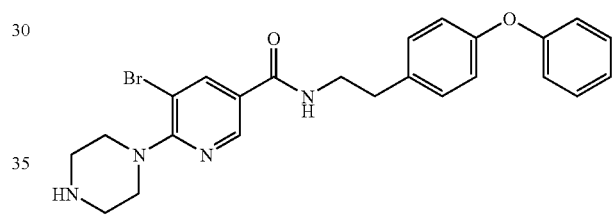

In analogy to example 26, 5-bromo-6-chloro-nicotinic acid methyl ester reacted with N-Boc-piperazine and then, using 4-phenoxyphenethylamine in the coupling step, converted to 5-bromo-N-[2-(4-phenoxy-phenyl)-ethyl]-6-piperazin-1-yl-nicotinamide. Off-white solid. MS (ISP): 481.0 ([M+H]⁺)

Example 35

N-[2-(4-Chloro-phenyl)-ethyl]-6-(4-methyl-piperazin-1-yl)-4-trifluoromethyl-nicotinamide

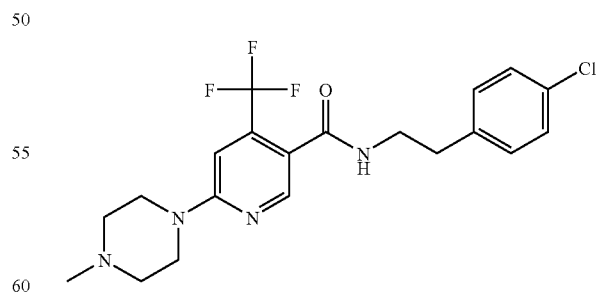

In analogy to example 1 methyl 6-chloro-4-(trifluoromethyl)nicotinate was reacted with N-methylpiperazine and then, using 4-chlorophenethylamine in the coupling step, converted to N-[2-(4-chloro-phenyl)-ethyl]-6-(4-methyl-piperazin-1-yl)-4-trifluoro-methyl-nicotinamide. Off-white solid. MS (ISP): 427.2 ([M+H]⁺)

Example 36

6-(4-Methyl-piperazin-1-yl)-N-[2-(4-phenoxy-phenyl)-ethyl]-4-trifluoromethyl-nicotinamide

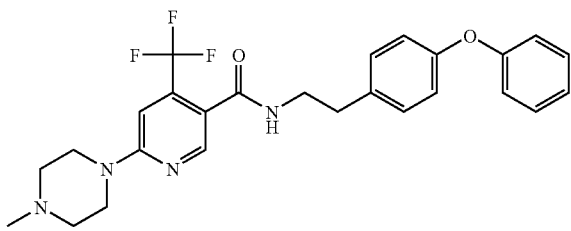

In analogy to example 1 methyl 6-chloro-4-(trifluoromethyl)nicotinate was reacted with N-methylpiperazine and then, using 4-phenoxyphenethylamine in the coupling step, converted to 6-(4-methyl-piperazin-1-yl)-N-[2-(4-phenoxyphenyl)-ethyl]-4-trifluoro-methyl-nicotinamide. Off-white solid. MS (ISP): 485.2 ([M+H]$^+$)

Example 37

2-Chloro-6-(4-methyl-piperazin-1-yl)-N-[2-(4-phenoxy-phenyl)-ethyl]-nicotinamide

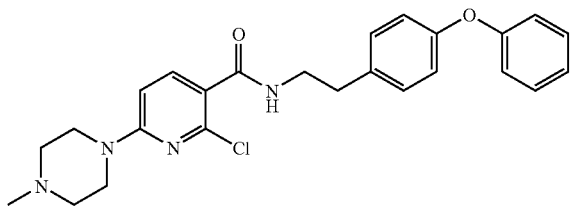

In analogy to example 21 methyl 2,6-dichloronicotinic acid was coupled with 4-phenoxyphenethylamine and then reacted with N-methylpiperazine. Yellow solid.
MS (ISP): 451.0 ([M+H]$^+$)

Example 38

2-Chloro-N-[2-(4-chloro-phenyl)-ethyl]-6-piperazin-1-yl-nicotinamide a) 4-{6-Chloro-5-[2-(4-chloro-phenyl)-ethylcarbamoyl]-pyridin-2-yl}-piperazine-1-carbo-xylic acid tert-butyl ester

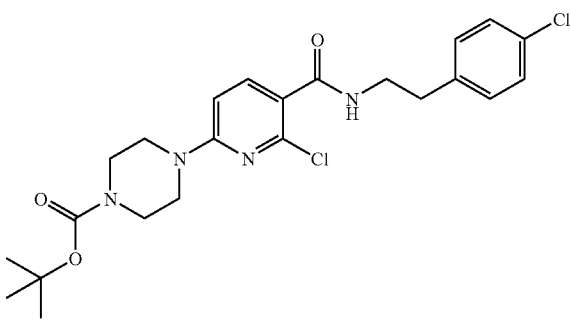

In analogy to example 38 methyl 2,6-dichloronicotinic acid was coupled with 4-chlorophenethylamine and then reacted with N-Boc-piperazine. Light yellow solid.
MS (ISP): 479.0 ([M+H]$^+$)

b) 2-Chloro-N-[2-(4-chloro-phenyl)-ethyl]-6-piperazin-1-yl-nicotinamide

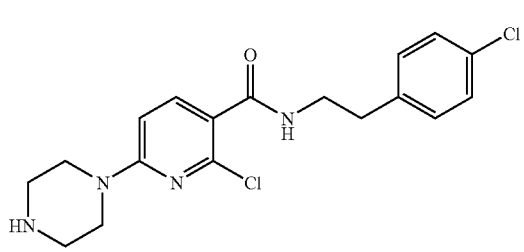

In analogy to example 4.b 4-{6-chloro-5-[2-(4-chlorophenyl)-ethylcarbamoyl]-pyridin-2-yl}-piperazine-1-carboxylic acid tert-butyl ester was converted to 2-chloro-N-[2-(4-chloro-phenyl)-ethyl]-6-piperazin-1-yl-nicotinamide. Light yellow solid.
MS (ISP): 379.2 ([M+H]$^+$)

Example 39

2-Chloro-N-[2-(4-phenoxy-phenyl)-ethyl]-6-piperazin-1-yl-nicotinamide a) 4-{6-Chloro-5-[2-(4-phenoxy-phenyl)-ethylcarbamoyl]-pyridin-2-yl}-piperazine-1-car-boxylic acid tert-butyl ester

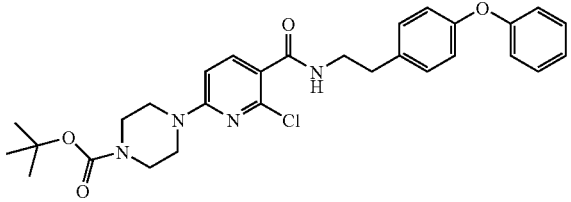

In analogy to example 38 methyl 2,6-dichloronicotinic acid was coupled with 4-phenoxyphenethylamine and then reacted with N-Boc-piperazine. Yellow solid.
MS (ISP): 537.0 ([M+H]$^+$)

b) 2-Chloro-N-[2-(4-phenoxy-phenyl)-ethyl]-6-piperazin-1-yl-nicotinamide

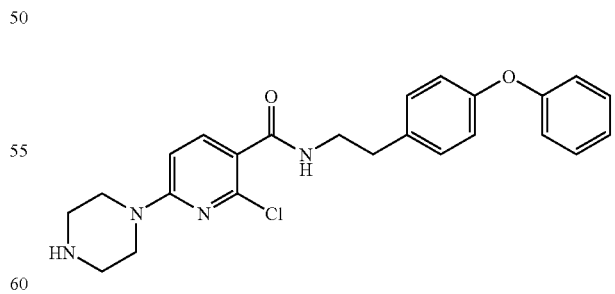

In analogy to example 4.b 4-{6-chloro-5-[2-(4-phenoxyphenyl)-ethylcarbamoyl]-pyridin-2-yl}-piperazine-1-carboxylic acid tert-butyl ester was converted to 2-chloro-N-[2-(4-phenoxy-phenyl)-ethyl]-6-piperazin-1-yl-nicotinamide. Off-white solid.
MS (ISP): 437.1 ([M+H]$^+$).

Example 40 rac-N-[1-(3,4-Dichloro-phenyl)-ethyl]-3-fluoro-benzamide

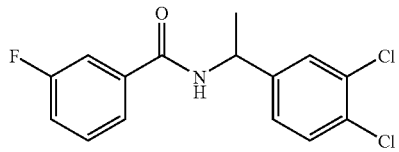

To a solution of 143.8 mg (0.75 mmol) N-(3-dimethylaminopropyl)-N'-ethylcarbodiimide hydrochloride (EDC.HCl) and 91.6 mg (0.75 mmol) 4-dimethylaminopyridine (DMAP) in 1.5 ml dichloromethane were added 142 mg (0.75 mmol) rac-1-(3,4-dichloro-phenyl)-ethylamine and the solution stirred at ambient temperature for 5 min. To this solution were added 70 mg (0.5 mmol) 3-fluoro-benzoic acid and the mixture stirred at ambient temperature for 5 hours.

The reaction mixture was filtered through a cartridge filled with 2 g SCX/silica gel 1:1, pre-washed with 20 ml methanol and 20 ml dichloromethane, and the reaction product eluted with 20 ml dichloromethane. After evaporation rac-N-[1-(3,4-dichloro-phenyl)-ethyl]-3-fluoro-benzamide was obtained as colorless solid, MS (ISP): 311.9 and 314.0 ((M+H)$^{+\cdot}$).

Example 41

N-[2-(3,4-Dichloro-phenyl)-ethyl]-3-fluoro-benzamide

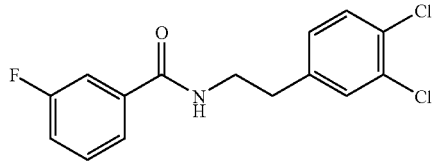

N-[2-(3,4-Dichloro-phenyl)-ethyl]-3-fluoro-benzamide was prepared in analogy to Example 40 from 3-fluoro-benzoic acid and 2-(3,4-dichloro-phenyl)-ethylamine: yellow solid,
MS (ISP): 311.9 and 314.0 ((M+H)$^{+\cdot}$).

Example 42

6-(2-Methoxy-ethylamino)-N-[2-(4-phenoxy-phenyl)-ethyl]-nicotinamide

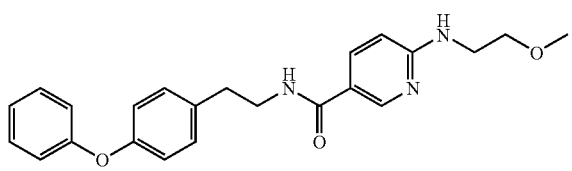

The title compound was prepared in analogy to example 1, but using 2-methoxy-ethylamine in the first step and 2-(4-phenoxy-phenyl)-ethylamine in the third step.
MS (ISP): 392.2 ((M+H)$^{+\cdot}$).

Example 43

N-[2-(3-Chloro-phenyl)-ethyl]-6-(2-methoxy-ethylamino)-nicotinamide

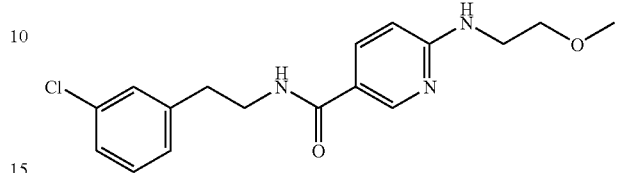

The title compound was prepared in analogy to example 1, but using 2-methoxy-ethylamine in the first step and 2-(3-chloro-phenyl)-ethylamine in the third step.

Example 44

N-[2-(3-Chloro-phenyl)-ethyl]-6-[4-(2-methoxy-phenyl)-piperazin-1-yl]-nicotinamide

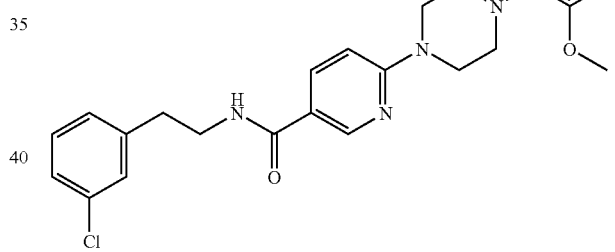

The title compound was prepared in analogy to example 1, but using 1-(2-methoxyphenyl)piperazine in the first step and 2-(3-chloro-phenyl)-ethylamine in the third step.

Example 45

6-[2-(3-Chloro-phenyl)-ethylamino]-N-(2-pyridin-2-yl-ethyl)-nicotinamide

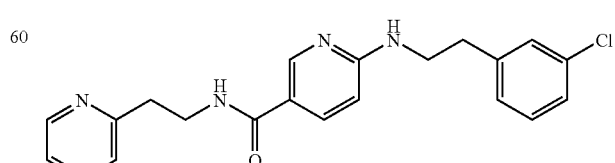

The title compound was prepared in analogy to example 1 but using 2-(3-chloro-phenyl)-ethylamine in the first step and 2-pyridin-2-yl-ethylamine in the third step.

Example 46

6-[2-(3-Chloro-phenyl)-ethylamino]-N-(2-pyridin-4-yl-ethyl)-nicotinamide

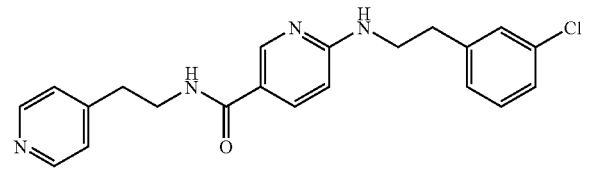

The title compound was prepared in analogy to example 1, but using 2-(3-chloro-phenyl)-ethylamine in the first step and 2-pyridin-4-yl-ethylamine in the third step.

Example 47

N-Phenethyl-6-[(pyridin-2-ylmethyl)-amino]-nicotinamide

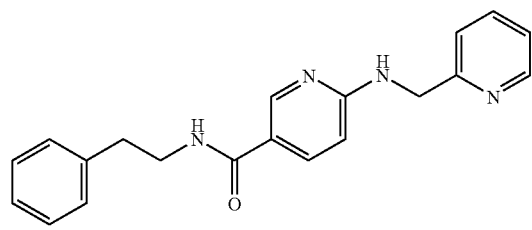

The title compound was prepared in analogy to example 1, but using 2-(aminomethyl)pyridine in the first step and phenethylamine in the third step.
MS (ISP): 333.2 ((M+H)$^+$).

Example 48

6-Phenylamino-N-(3-phenyl-propyl)-nicotinamide

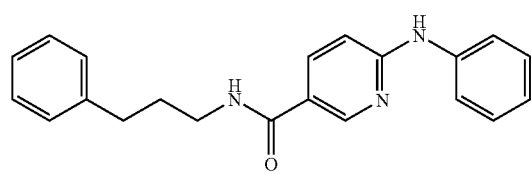

The title compound was prepared in analogy to example 1, but starting from 6-phenylamino-nicotinic acid and using 3-phenyl-propylamine in the third step.

Example 49

6-[2-(3-Chloro-phenyl)-ethylamino]-N-(3-phenyl-propyl)-nicotinamide

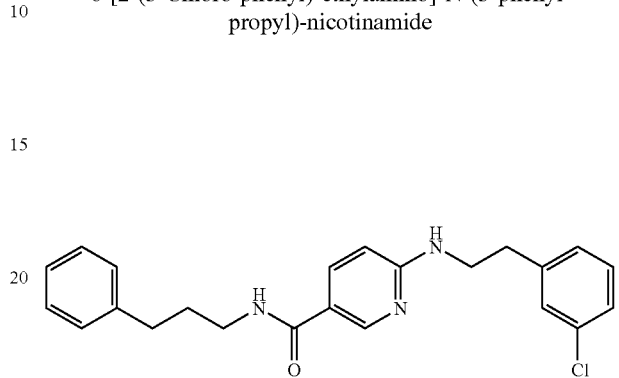

The title compound was prepared in analogy to example 1, but using 2-(3-chloro-phenyl)-ethylamine in the first step and 3-phenyl-propylamine in the third step.

Example 50

2-(3-Morpholin-4-yl-propylamino)-N-phenethyl-nicotinamide

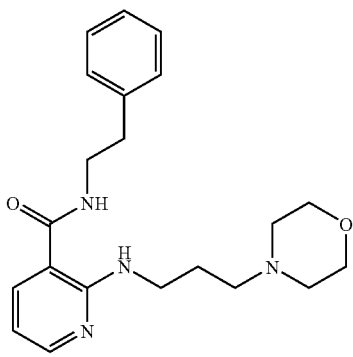

The title compound was prepared in analogy to example 1, but starting from 2-chloro-nicotinic acid methyl ester and subsequently using 3-morpholin-4-yl-propylamine in the first step and phenethylamine in the third step.

Example 51

2-(4-Methanesulfonyl-piperazin-1-yl)-N-[2-(4-phenoxy-phenyl)-ethyl]-nicotinamide

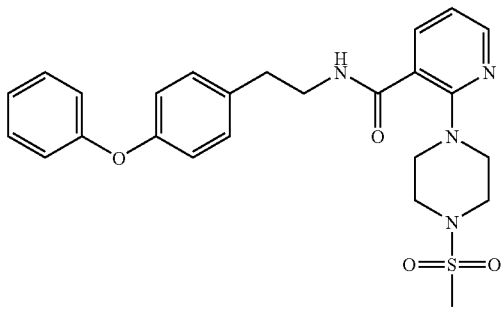

The title compound was prepared in analogy to example 1, but starting from 2-chloro-nicotinic acid methyl ester and subsequently using 1-methanesulfonyl-piperazine in the first step and 2-(4-phenoxy-phenyl)-ethylamine in the third step. MS (ISP): 481.1 ((M+H)$^{+\cdot}$).

Example 52

N-(2-Biphenyl-4-yl-ethyl)-2-(3-morpholin-4-yl-propylamino)-nicotinamide

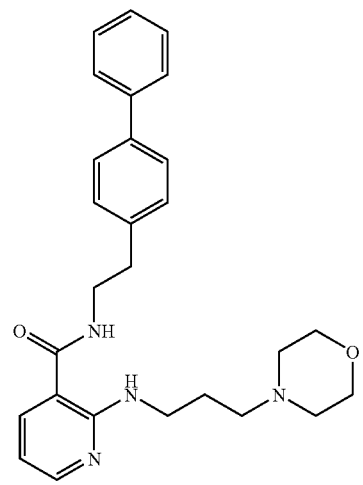

The title compound was prepared in analogy to example 1, but starting from 2-chloro-nicotinic acid methyl ester and subsequently using 3-morpholin-4-yl-propylamine in the first step and 2-biphenyl-4-yl-ethylamine in the third step.

Example 53

N-[2-(2-Fluoro-phenyl)-ethyl]-4-(2-methyl-benzoimidazol-1-ylmethyl)-benzamide

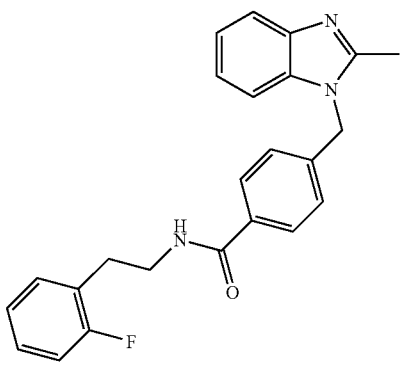

The title compound was prepared in analogy to example 1c, but using 2-(2-fluoro-phenyl)-ethylamine and 4-(2-methyl-benzoimidazol-1-ylmethyl)-benzoic acid as coupling components. MS (ISP): 388.2 ((M+H)$^{+\cdot}$).

Example 54

N-(2-Cyclohexyl-ethyl)-6-(4-methyl-piperazin-1-yl)-nicotinamide

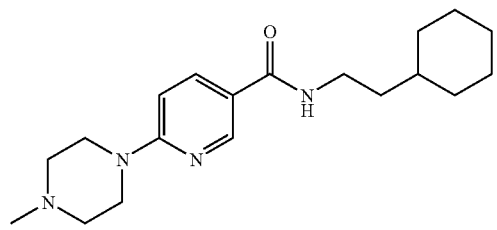

The title compound was prepared in analogy to example 1c, but using 2-cyclohexyl-ethylamine as amine component in the coupling reaction. Off-white solid. MS (ISP): 331.4 ((M+H)+).

Example 55

N-Cyclohexylmethyl-6-(4-methyl-piperazin-1-yl)-nicotinamide

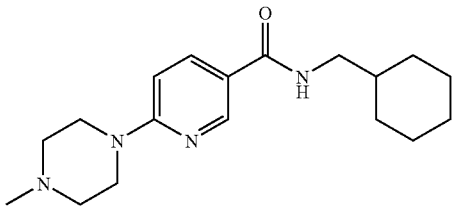

The title compound was prepared in analogy to example 1c, but using cyclohexyl-methylamine as amine component in the coupling reaction. Off-white solid. MS (ISP): 317.3 ((M+H)+).

Examples A-E

Additionally the following known compounds were prepared as TAAR1 ligands using procedures analogous to those describe above:
A: 6-(4-methyl-piperazin-1-yl)-N-phenethyl-nicotinamide (CAS 199478-31-4)
B: N-(3,4-dichloro-benzyl)-3-fluoro-benzamide (CAS 424815-98-5)
C: N-(4-chloro-benzyl)-3-fluoro-benzamide (CAS 544661-83-8)
D: N-(3-chloro-benzyl)-3-fluoro-benzamide (CAS 796051-07-5)
E: N-phenethyl-6-phenylamino-nicotinamide (CAS 571913-74-1).

The invention claimed is:
1. A compound having formula IA

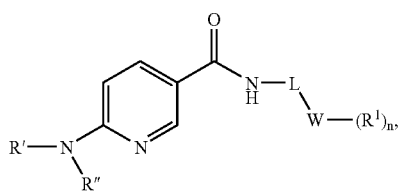

wherein
R$^1$ is hydrogen, halogen, lower alkyl, lower alkoxy, lower alkyl substituted by halogen,
—O—(CH$_2$)$_p$-aryl or aryl;
R' and R" together with the N atom to which they are attached form a piperazine group optionally substituted by methyl —CH$_2$-cycloalkyl, —(CH$_2$)$_p$—O-lower alkyl or by substituted aryl wherein the substitution on aryl is lower alkyl or lower alkoxy
W is phenyl, benzo[1,3]dioxolyl, pyridine-2, 3- or 4-yl, indolyl or cycloalkyl;
L is —CH(CH$_3$)—, —CH$_2$CH$_2$—, —CH$_2$CH(CH$_3$)—,
n is 1 or 2; in case n is 2, R$^1$ may be the same or different;
p is 0, 1, 2 or 3,
or a pharmaceutically suitable acid addition salt thereof, with the exception of the following compound
6-(4-methyl-piperazin-1-yl)-N-phenethyl-nicotinamide.
2. A compound of claim 1, wherein the piperazine group is 4-methyl-piperazin-1-yl.
3. A compound of claim 2, selected from the group consisting of
N[2-(4-chloro-phenyl)-ethyl]-6-(4-methyl-piperazin-1-yl)-nicotinamide,
N[2-(3-chloro-phenyl)-ethyl]-6-(4-methyl-piperazin-1-yl)-nicotinamide,
6-(4-methyl-piperazin-1-yl)-N-[2-(3-trifluoromethyl-phenyl)-ethyl]-nicotinamide,
N[2-(4-methoxy-phenyl)-ethyl]-6-(4-methyl-piperazin-1-yl)-nicotinamide,
N[2-(3-methoxy-phenyl)-ethyl]-6-(4-methyl-piperazin-1-yl)-nicotinamide,
N-(2-benzo[1,3]dioxo-5-yl-ethyl)-6-(4-methyl-piperazin-1-yl)-nicotinamide,
N-(2-biphenyl-4-yl-ethyl)-6-(4-methyl-piperazin-1-yl)-nicotinamide,
6-(4-methyl-piperazin-1-yl)-N-[2-(4-phenoxy-phenyl)-ethyl]-nicotinamide,
6-(4-methyl-piperazin-1-yl)-N-[2-(3-phenoxy-phenyl)-ethyl]-nicotinamide,
N[2-(4-benzyloxy-phenyl)-ethyl]-6-(4-methyl-piperazin-1-yl)-nicotinamide,
N-[2-(1-methyl-1H-indo-3-yl)-ethyl]-6-(4-methyl-piperazin-1-yl)-nicotinamide,
N-(2-cyclohexyl-ethyl)-6-(4-methyl-piperazin-1-yl)-nicotinamide, and
N-cyclohexyl-methyl-6-(4-methyl-piperazin-1-yl)-nicotinamide.
4. A compound of claim 1, wherein the piperazine group is piperazin-1-yl.
5. A compound of claim 4, selected from the group consisting of
N-[2-(4-chloro-phenyl)-ethyl]-6-piperazin-1-yl-nicotinamide,
N-[2-(4-phenoxy-phenyl)-ethyl]-6-piperazin-1-yl-nicotinamide,
N-[2-(3-phenoxy-phenyl)-ethyl]-6-piperazin-1-yl-nicotinamide, and
N-[2-(4-benzyloxy-phenyl)-ethyl]-6-piperazin-1-yl-nicotinamide.
6. A compound of formula

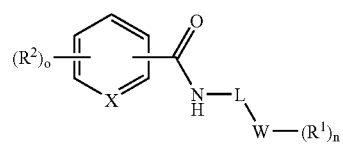

wherein
R$^1$ is hydrogen, halogen, lower alkyl, lower alkoxy, lower alkyl substituted by halogen,
—O—(CH$_2$)$_p$-aryl or aryl;
o is 2; and one R$^2$ is NR'R" and the other R$^2$ is halogen, wherein
R' and R" together with the N atom to which they are attached form a piperazine group optionally substituted by lower alkyl, —CH$_2$-cycloalkyl, —S(O)$_2$CH$_3$, —(CH$_2$)$_p$—O-lower alkyl or by substituted aryl wherein the substitution on aryl is lower alkyl or lower alkoxy;

W is phenyl, benzo[1,3]dioxolyl, pyridine-2, 3- or 4-yl, indolyl or cycloalkyl;

L is —CH$_2$—, —CH(CH$_3$)—, —CH$_2$CH$_2$—, —CH$_2$CH(CH$_3$)— or —CH$_2$CH$_2$CH$_2$—;

X is N;

n is 1 or 2; in case n is 2, each R$^1$ can be the same or different; and p is 0, 1, 2 or 3;

or a pharmaceutically suitable acid addition salt thereof.

7. A compound of claim 6, selected from the group consisting of 5-bromo-N-[2-(4-chloro-phenyl)-ethyl]-6-(4-methyl-piperazin-1-yl)-nicotinamide, 5-bromo-6-(4-methyl-piperazin-1-yl)-N-[2-(4-phenoxy-phenyl)-ethyl]-nicotinamide, 5-bromo-N-[2-(4-chloro-phenyl)-ethyl]-6-piperazin-1-yl-nicotinamide, and 5-bromo-N-[2-(4-phenoxy-phenyl)-ethyl]-6-piperazin-1-yl-nicotinamide.

8. A compound of claim 1, wherein W is phenyl.

9. A pharmaceutical composition comprising a therapeutically effective amount of a compound of formula IA

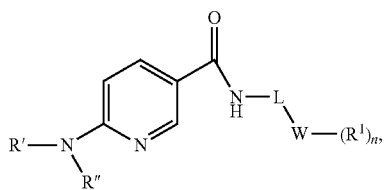

IA wherein

R$^1$ is hydrogen, halogen, lower alkyl, lower alkoxy, lower alkyl substituted by halogen,
—O—(CH$_2$)$_p$-aryl or aryl;

R'R" together with the N atom to which they are attached form a heterocycloalkyl group optionally substituted by lower alkyl, —CH$_2$- cycloalkyl, —(CH$_2$)$_p$—O-lower alkyl or by substituted aryl wherein the substitution on aryl is lower alkyl or lower alkoxy;

W is phenyl, benzo[1,3]dioxolyl, pyridine-2, 3- or 4-yl, indolyl or cycloalkyl;

L is —CH$_2$—, —CH(CH$_3$)—, —CH$_2$CH$_2$—, or —CH$_2$CH(CH$_3$)—;

X is N;

n is 1 or 2; in case n is 2, each R$^1$ can be the same or different;

o is 1; and p is 0, 1, 2 or 3;

or a pharmaceutically suitable acid addition salt thereof, with the exception of the following compound 6-(4-methyl-piperazin-1-yl)-N-phenethyl-nicotinamide, and a pharmaceutically acceptable carrier.

10. A pharmaceutical composition comprising a therapeutically effective amount of a compound of formula I

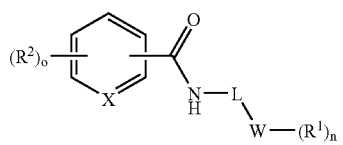

I wherein

R$^1$ is hydrogen, halogen, lower alkyl, lower alkoxy, lower alkyl substituted by halogen,
—O—(CH$_2$)$_p$-aryl or aryl;

o is 2; and one R$^2$ is NR'R" and the other R$^2$ is halogen, wherein

R' and R" together with the N atom to which they are attached form a piperazine group optionally substituted by lower alkyl, —CH$_2$-cycloalkyl, —S(O)$_2$CH$_3$, —(CH$_2$)$_p$—O-lower alkyl or by substituted aryl wherein the substitution on aryl is lower alkyl or lower alkoxy;

W is phenyl, benzo[1,3]dioxolyl, pyridine-2, 3- or 4-yl, indolyl or cycloalkyl;

L is —CH$_2$—, —CH(CH$_3$)—, —CH$_2$CH$_2$—, —CH$_2$CH(CH$_3$)— or —CH$_2$CH$_2$CH$_2$—;

X is N;

n is 1 or 2; in case n is 2, each R$^1$ can be the same or different; and p is 0, 1, 2 or 3;

or a pharmaceutically suitable acid addition salt thereof and a pharmaceutically acceptable carrier.

* * * * *